US012594166B2

(12) United States Patent
Gordon et al.

(10) Patent No.: US 12,594,166 B2
(45) Date of Patent: Apr. 7, 2026

(54) METHOD FOR MANUFACTURING A LOW-PROFILE INTERCRANIAL DEVICE AND THE LOW-PROFILE INTERCRANIAL DEVICE MANUFACTURED THEREBY

(71) Applicants:Longeviti Neuro Solutions, Inc., Baltimore, MD (US); THE JOHNS HOPKINS UNIVERSITY, Baltimore, MD (US)

(72) Inventors: Chad R. Gordon, Cockeysville, MD (US); Jesse Christopher, Hunt Valley, MD (US)

(73) Assignee: Longeviti Neuro Solutions, Inc., Baltimore, MD (US)

( * ) Notice: Subject to any disclaimer, the term of this patent is extended or adjusted under 35 U.S.C. 154(b) by 788 days.

(21) Appl. No.: 17/344,518

(22) Filed: Jun. 10, 2021

(65) Prior Publication Data

US 2021/0298905 A1    Sep. 30, 2021

Related U.S. Application Data

(63) Continuation of application No. 17/127,049, filed on Dec. 18, 2020, now Pat. No. 11,446,148, which is a continuation of application No. 15/669,268, filed on Aug. 4, 2017, now Pat. No. 10,912,648.

(60) Provisional application No. 62/381,242, filed on Aug. 30, 2016.

(51) Int. Cl.
    *A61F 2/28*        (2006.01)
(52) U.S. Cl.
    CPC ................................. *A61F 2/2875* (2013.01)

(58) Field of Classification Search
    CPC .. A61F 2/2875; A61B 17/688; A61N 1/37514
    See application file for complete search history.

(56) References Cited

U.S. PATENT DOCUMENTS

| | | | |
|---|---|---|---|
| 4,206,762 | A | 6/1980 | Cosman |
| 4,281,666 | A | 8/1981 | Cosman |
| 4,436,684 | A | 3/1984 | White |
| 4,660,568 | A | 4/1987 | Cosman |
| 4,805,634 | A | 2/1989 | Ullrich et al. |
| 5,218,975 | A | 6/1993 | Prostkoff |
| 5,503,164 | A | 4/1996 | Friedman |

(Continued)

FOREIGN PATENT DOCUMENTS

| | | |
|---|---|---|
| CN | 103598883 A | 2/2014 |
| JP | 2008194426 A | 8/2008 |

(Continued)

OTHER PUBLICATIONS

Ledesma et al., Responsive Neurostimulation System (RNS) in setting of cranioplasty and history of multiple craniotomies, Interdisciplinary Neurosurgery, vol. 5, Sep. 2016, pp. 29-31.

(Continued)

*Primary Examiner* — Melanie R Tyson
(74) *Attorney, Agent, or Firm* — Welsh Flaxman & Flaxman LLC

(57) ABSTRACT

A low-profile intercranial device including a low-profile static cranial implant and a functional neurosurgical implant. The low-profile static cranial implant and the functional neurosurgical implant are virtually designed and interdigitated prior to physical assembly of the low-profile intercranial device.

12 Claims, 10 Drawing Sheets

(56) References Cited

U.S. PATENT DOCUMENTS

| | | | |
|---|---|---|---|
| 5,741,215 A | 4/1998 | D'Urso | |
| 6,006,124 A | 12/1999 | Fischell et al. | |
| 6,016,449 A | 1/2000 | Fischell et al. | |
| 6,061,593 A | 5/2000 | Fischell et al. | |
| 6,176,879 B1 | 1/2001 | Reischl et al. | |
| 6,248,126 B1 | 6/2001 | Lesser et al. | |
| 6,354,299 B1 | 3/2002 | Fischell et al. | |
| 6,366,813 B1 | 4/2002 | DiLorenzo | |
| 6,427,086 B1 | 7/2002 | Fischell et al. | |
| 6,485,464 B1 | 11/2002 | Christensen et al. | |
| 6,560,486 B1 | 5/2003 | Osorio et al. | |
| 6,618,623 B1 | 9/2003 | Pless | |
| 6,726,678 B1 | 4/2004 | Nelson et al. | |
| 6,819,956 B2 | 11/2004 | DiLorenzo | |
| 6,882,881 B1 | 4/2005 | Lesser et al. | |
| 6,931,284 B2 | 8/2005 | Engmark et al. | |
| 6,932,842 B1 | 8/2005 | Itschko et al. | |
| 7,050,877 B2 | 5/2006 | Iseki et al. | |
| 7,113,841 B2 | 9/2006 | Abe et al. | |
| 7,158,833 B2 | 1/2007 | Pless et al. | |
| 7,209,787 B2 | 4/2007 | DiLorenzo | |
| 7,212,864 B2 | 5/2007 | Wahlstrand et al. | |
| 7,231,254 B2 | 6/2007 | DiLorenzo | |
| 7,242,982 B2 | 7/2007 | Singhal et al. | |
| 7,242,984 B2 | 7/2007 | DiLorenzo | |
| 7,263,401 B2 | 8/2007 | Scott et al. | |
| 7,277,758 B2 | 10/2007 | DiLorenzo | |
| 7,324,851 B1 | 1/2008 | DiLorenzo | |
| 7,346,391 B1 | 3/2008 | Osorio et al. | |
| 7,346,397 B2 | 3/2008 | Money et al. | |
| 7,392,089 B2 | 6/2008 | Wahlstrand et al. | |
| 7,529,586 B2 | 5/2009 | Wahlstrand et al. | |
| 7,565,199 B2 | 7/2009 | Sheffield et al. | |
| 7,596,399 B2 | 9/2009 | Singhal et al. | |
| 7,596,408 B2 | 9/2009 | Singhal et al. | |
| 7,647,097 B2 | 1/2010 | Flaherty et al. | |
| 7,657,316 B2 | 2/2010 | Jaax et al. | |
| 7,684,866 B2 | 3/2010 | Fowler et al. | |
| 7,747,305 B2 | 6/2010 | Dean et al. | |
| 7,747,318 B2 | 6/2010 | John et al. | |
| 7,844,345 B2 | 11/2010 | Boling et al. | |
| 7,848,817 B2 | 12/2010 | Janzig et al. | |
| 7,887,501 B2 | 2/2011 | Riordan et al. | |
| 7,894,905 B2 | 2/2011 | Pless et al. | |
| 7,918,887 B2 | 4/2011 | Roche | |
| 7,935,858 B2 | 5/2011 | Praetzal | |
| 8,086,336 B2 | 12/2011 | Christensen | |
| 8,116,875 B2 | 2/2012 | Osypka et al. | |
| 8,182,540 B2 | 5/2012 | Lin et al. | |
| 8,202,090 B2 | 6/2012 | Shachar | |
| 8,235,903 B2 | 8/2012 | Abraham | |
| 8,306,607 B1 | 11/2012 | Levi et al. | |
| 8,397,732 B2 | 3/2013 | Singhal et al. | |
| 8,454,701 B2 | 6/2013 | Devauchelle et al. | |
| 8,457,744 B2 | 6/2013 | Janzig et al. | |
| 8,591,562 B2 | 11/2013 | D'Ambrosio et al. | |
| 8,706,285 B2 | 4/2014 | Narainasamy et al. | |
| 8,761,889 B2 | 6/2014 | Wingeier et al. | |
| 8,781,557 B2 | 7/2014 | Pean et al. | |
| 8,938,290 B2 | 1/2015 | Wingeier et al. | |
| D723,162 S | 2/2015 | Brogan et al. | |
| 8,956,418 B2 | 2/2015 | Wasielewski et al. | |
| 8,965,513 B2 | 2/2015 | Wingeier et al. | |
| 9,014,810 B2 | 4/2015 | Sauter-Starace et al. | |
| 9,044,195 B2 * | 6/2015 | Manwaring | A61B 8/4209 |
| 9,084,901 B2 | 7/2015 | Wahlstrand | |
| 9,101,341 B2 | 8/2015 | Fitzgerald et al. | |
| 9,149,564 B2 | 10/2015 | Jin et al. | |
| 9,162,072 B2 | 10/2015 | Singhal et al. | |
| 9,167,976 B2 | 10/2015 | Wingeier et al. | |
| 9,167,977 B2 | 10/2015 | Wingeier et al. | |
| 9,167,978 B2 | 10/2015 | Wingeier et al. | |
| 9,179,850 B2 | 11/2015 | Wingeier et al. | |
| 9,216,084 B2 | 12/2015 | Gordon et al. | |
| 9,289,143 B2 | 3/2016 | Wingeier et al. | |
| 9,375,564 B2 | 6/2016 | Wingeier et al. | |
| 9,387,320 B2 | 7/2016 | Wingeier et al. | |
| 9,393,432 B2 | 7/2016 | Wahlstrand et al. | |
| 9,421,363 B2 | 8/2016 | Krahl et al. | |
| 9,421,371 B2 | 8/2016 | Pless et al. | |
| 9,440,064 B2 | 9/2016 | Wingeier et al. | |
| 9,462,958 B2 | 10/2016 | Osorio et al. | |
| 9,474,611 B2 | 10/2016 | Restrepo et al. | |
| 9,522,081 B2 | 12/2016 | D'Ambrosio et al. | |
| 9,573,322 B2 | 2/2017 | Wasielewski | |
| 9,592,124 B2 | 3/2017 | Joganic | |
| 9,592,377 B2 | 3/2017 | Greenberg et al. | |
| 9,993,337 B1 * | 6/2018 | Brogan | A61F 2/2875 |
| 10,588,710 B2 | 3/2020 | Van Venrooij et al. | |
| 2002/0002390 A1 | 1/2002 | Fischell et al. | |
| 2002/0169485 A1 | 11/2002 | Pless et al. | |
| 2003/0125786 A1 | 7/2003 | Gliner et al. | |
| 2004/0034368 A1 * | 2/2004 | Pless | A61N 1/37518 |
| | | | 606/129 |
| 2004/0172090 A1 | 9/2004 | Janzig et al. | |
| 2004/0176816 A1 | 9/2004 | Singhal et al. | |
| 2004/0176818 A1 | 9/2004 | Wahlstrand et al. | |
| 2004/0267234 A1 | 12/2004 | Heart et al. | |
| 2005/0003268 A1 | 1/2005 | Scott et al. | |
| 2005/0004620 A1 | 1/2005 | Singhal et al. | |
| 2005/0004637 A1 | 1/2005 | Singhal et al. | |
| 2005/0043835 A1 | 2/2005 | Christensen | |
| 2005/0203366 A1 | 9/2005 | Donoghue et al. | |
| 2005/0245984 A1 | 11/2005 | Singhal et al. | |
| 2007/0129652 A1 * | 6/2007 | Nita | A61B 5/4076 |
| | | | 601/2 |
| 2007/0179558 A1 | 8/2007 | Gliner et al. | |
| 2007/0225773 A1 | 9/2007 | Shen et al. | |
| 2009/0112278 A1 | 4/2009 | Wingeier et al. | |
| 2009/0281623 A1 | 11/2009 | Kast et al. | |
| 2010/0145162 A1 * | 6/2010 | Devauchelle | A61N 1/375 |
| | | | 600/300 |
| 2010/0292963 A1 | 11/2010 | Schroeder | |
| 2011/0066072 A1 | 3/2011 | Kawoos et al. | |
| 2011/0213382 A1 | 9/2011 | Decre et al. | |
| 2012/0063655 A1 | 3/2012 | Dean et al. | |
| 2012/0259428 A1 | 10/2012 | Brogan et al. | |
| 2013/0204316 A1 | 8/2013 | Carpentier et al. | |
| 2013/0247644 A1 | 9/2013 | Swoboda et al. | |
| 2013/0282011 A1 | 10/2013 | Brogan et al. | |
| 2014/0249454 A1 | 9/2014 | Carpentier | |
| 2014/0309744 A1 | 10/2014 | Batty et al. | |
| 2014/0330123 A1 * | 11/2014 | Manwaring | A61B 8/4444 |
| | | | 600/443 |
| 2014/0343350 A1 | 11/2014 | Martinson et al. | |
| 2014/0350635 A1 | 11/2014 | Strother et al. | |
| 2014/0378783 A1 | 12/2014 | Ledet et al. | |
| 2015/0038948 A1 | 2/2015 | Ludvig et al. | |
| 2015/0051455 A1 | 2/2015 | Wasielewski et al. | |
| 2015/0105858 A1 | 4/2015 | Papay et al. | |
| 2015/0157862 A1 | 6/2015 | Greenberg et al. | |
| 2015/0231594 A1 | 8/2015 | Aguilar-Mendoza et al. | |
| 2015/0289980 A1 * | 10/2015 | Hirata | G05B 19/4097 |
| | | | 700/98 |
| 2015/0328004 A1 | 11/2015 | Mafhouz | |
| 2015/0351915 A1 | 12/2015 | DeFelice et al. | |
| 2016/0007874 A1 | 1/2016 | Ma et al. | |
| 2016/0045723 A1 | 2/2016 | Bornzin et al. | |
| 2016/0083573 A1 | 3/2016 | Berdin et al. | |
| 2016/0184100 A1 | 6/2016 | Jorganic | |
| 2016/0185046 A1 | 6/2016 | Littlefield | |
| 2016/0193048 A1 * | 7/2016 | Prada | A61F 2/2875 |
| | | | 623/17.19 |
| 2016/0263277 A1 | 9/2016 | Kim et al. | |
| 2016/0296312 A1 | 10/2016 | Kuhn et al. | |
| 2016/0346091 A1 | 12/2016 | Bin Abdul Rahman et al. | |
| 2017/0027629 A1 * | 2/2017 | Ackerman | A61F 2/4601 |
| 2017/0049351 A1 | 2/2017 | Esteller | |
| 2017/0049398 A1 | 2/2017 | Hirata et al. | |
| 2017/0156596 A1 | 6/2017 | Aguilar-Mendoza et al. | |
| 2017/0368330 A1 | 12/2017 | Silay et al. | |
| 2018/0185674 A1 | 7/2018 | Bauer et al. | |
| 2019/0030374 A1 * | 1/2019 | Carpentier | A61N 7/00 |
| 2020/0030099 A1 | 1/2020 | Sampath et al. | |

(56)    References Cited

U.S. PATENT DOCUMENTS

FOREIGN PATENT DOCUMENTS

| | | | | | |
|---|---|---|---|---|---|
| KR | 1020120088928 | A | 8/2012 | | |
| WO | 2004093725 | A2 | 11/2004 | | |
| WO | 2011036148 | A1 | 3/2011 | | |
| WO | 2012047759 | A1 | 4/2012 | | |
| WO | WO-2012063377 | A1 * | 5/2012 | .......... | A61B 17/688 |
| WO | 2012147114 | A1 | 11/2012 | | |
| WO | 2015081025 | A1 | 6/2015 | | |
| WO | 2015081027 | A1 | 6/2015 | | |
| WO | 2015081140 | A1 | 6/2015 | | |
| WO | 2015081177 | A1 | 6/2015 | | |
| WO | 2015081225 | A1 | 6/2015 | | |
| WO | 2015081232 | A1 | 6/2015 | | |
| WO | 2015081247 | A1 | 6/2015 | | |
| WO | 2015157554 | A1 | 10/2015 | | |
| WO | 2016086049 | A1 | 6/2016 | | |
| WO | 2016086054 | A1 | 6/2016 | | |
| WO | 2017039762 | A1 | 3/2017 | | |
| WO | 2017046300 | A1 | 3/2017 | | |
| WO | 2018076075 | A1 | 5/2018 | | |

OTHER PUBLICATIONS

Wei et al., Implant Site Infection and Bone Flap Osteomyelitis Associated with NeuroPace Responsive Neurotimulation System. World Neurosurg. Apr. 2016; 88:687.e1-6.
Sing, Mansher et al, "Countersinking" of reservoir in an irradiated patients can decrease tension on scalp closure, Surgical Neurology International, 2015; 6(Suppl 11): SS34-S.

* cited by examiner

112a

100

112a

100

114a

100

100

100

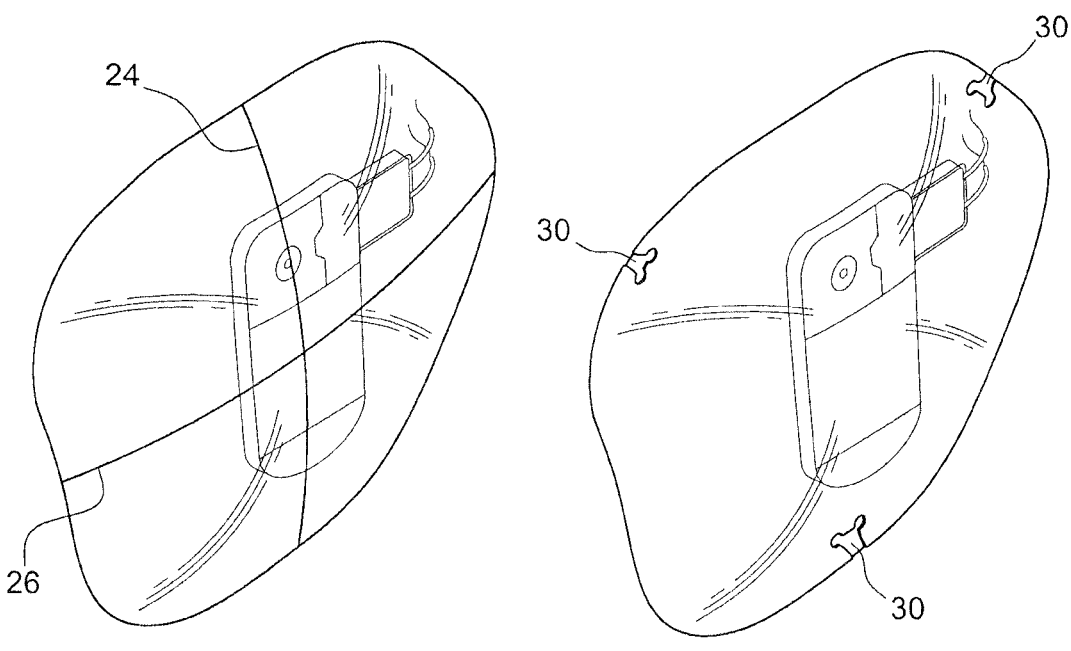
FIG. 13                  FIG. 14
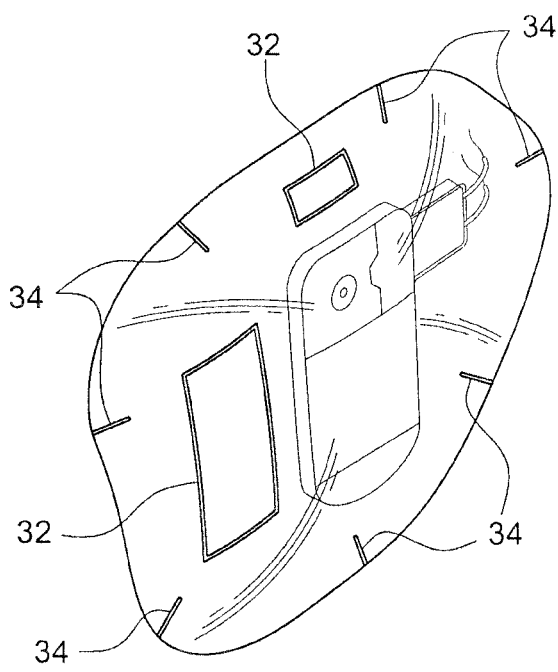
FIG. 15

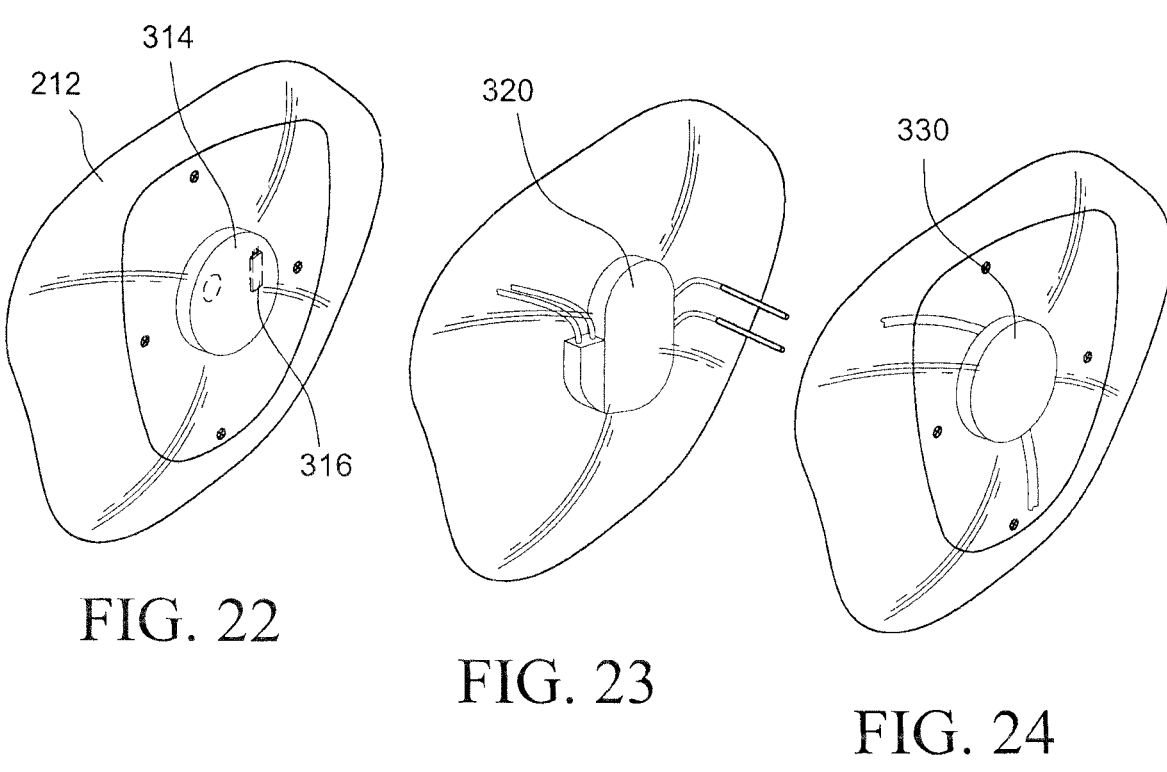
FIG. 22
FIG. 23
FIG. 24
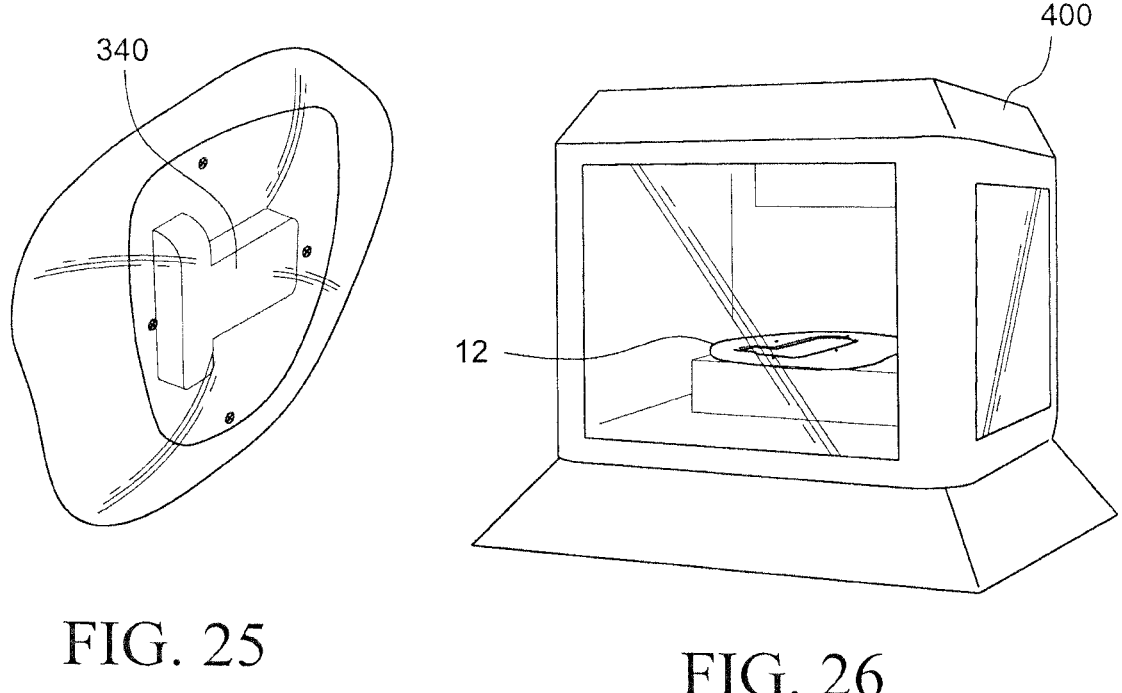
FIG. 25
FIG. 26

METHOD FOR MANUFACTURING A LOW-PROFILE INTERCRANIAL DEVICE AND THE LOW-PROFILE INTERCRANIAL DEVICE MANUFACTURED THEREBY

CROSS REFERENCE TO RELATED APPLICATION

This application is a continuation of U.S. patent application Ser. No. 17/127,049, entitled "METHOD FOR MANU-FACTURING A LOW-PROFILE INTERCRANIAL DEVICE AND THE LOW-PROFILE INTERCRANIAL DEVICE MANUFACTURED THEREBY" filed Dec. 18, 2020, which is currently pending, which is a continuation of U.S. patent application Ser. No. 15/669,268, entitled "METHOD FOR MANUFACTURING A LOW-PROFILE INTERCRANIAL DEVICE AND THE LOW-PROFILE INTERCRANIAL DEVICE MANUFACTURED THEREBY," filed Aug. 4, 2017, which issued as U.S. Pat. No. 10,912,648, which claims the benefit of U.S. Provisional Patent Application Ser. No. 62/381,242, entitled "METHOD FOR MANUFACTURING A LOW-PROFILE INTERCRA-NIAL DEVICE AND THE LOW-PROFILE INTERCRA-NIAL DEVICE MANUFACTURED THEREBY," filed Aug. 30, 2016, which are incorporated herein by reference.

BACKGROUND OF THE INVENTION

1. Field of the Invention

The present invention relates to intercranial devices and a virtual pre-operative method of interdigitating a customized static cranial implant and functional neurosurgical implant (s) for ideal anatomical placement together. More particularly, the present invention relates to a method for manu-facturing a low-profile intercranial device in a manner which minimizes abnormal shapes, visible contours, and/or cran-iofacial deformities, as well as the low-profile intercranial device resulting from the manufacturing method.

2. Description of the Related Art

During cranioplasty procedures, diseased or damaged portions of the skull (craniectomy defects) are safely removed and replaced, while the brain is exposed under-neath without injury. However, a similar operation could also be done in areas of normal, healthy cranial bone—in instances where a neuromodulation device is needed for implantation but the contour and appearance is challenging (and normal skull bone is removed and left off permanently in exchange for a cranial implant), such as in non-bearing scalp areas such as frontal or temporal regions. Following resection of diseased cranial bone (or normal bone in cosmetically-sensitive areas), such craniectomy defects are often reconstructed with custom craniofacial implants (CCIs)—as opposed to using generic, "off-the-shelf" mate-rials.

Historically, however, cranioplasty patients requesting custom craniofacial implant-based reconstruction for an ideal appearance have been limited to "second-stage" opera-tions in instances of pre-existing skull defects so that the exact fit and design could be obtained. However, recent modifications to the approach have allowed a few isolated surgical teams to perform "single-stage cranioplasties"—by which a clinician, such as a surgeon, manually reshapes/ resizes a previously-ordered, custom implant (with over-sized dimensions) to fit perfectly into the skull defect—as opposed to using "off-the-shelf" materials. Either way, for single-stage methods involving skull tumors or second-stage cranioplasties for pre-defined skull defects, the advent of computer-aided design/manufacturing (CAD/CAM), has provided surgeons with perfectly-shaped custom craniofa-cial implants designed and manufactured based in part on fine cut preoperative computed tomography (CT) scans and three-dimensional reconstruction (with or without stereo-lithographic models).

In fact, recent reports suggest that the use of custom craniofacial implants can improve cosmesis, decrease opera-tive times, prevent scalp-related wound complications, and enhance patient satisfaction—and therefore, they serve as an ideal medium for reconstructing neurosurgery patients. Similarly, all custom craniofacial implants up until now have been used to replace abnormal bone having some form of disease, either of benign or malignant etiology. These cus-tomized skull implants may be termed "static custom cran-iofacial implants"—mainly because their main constant (i.e., unchanged purpose with respect to time) purpose encom-passes strictly two benefits following placement—"brain protection" and "enhanced appearance".

Meanwhile, there are other "off-the-shelf" neurological implants that have functionality, such as delivering electrical impulses to interrupt seizure activity, but aren't customiz-able or designed to protect the brain. Most of these so-called functional neurological implants fall into two categories: Deep Brain Stimulators (DBS) and Cortical Brain Stimula-tors (CBS). Modern day neurologic devices are confronted and challenged with high extrusion and infection risk (i.e., current flaws in modern day devices lead to high incidence of extrusion through skin thereby requiring premature explantation) approaching 50%. Similarly, battery-powered, low-profile devices for intercranial placement currently do not exist on the market. As such, the field of neurosurgery has been hampered and limited in many areas including examples like battery-powered neuromodulation cortical stimulation and delivery of neurological medicines.

But with increasing experience and surgical complication rates exceedingly low, the custom craniofacial implants can also be modified in real-time for scenarios where more or less skull bone is removed and the skull defect dimensions do NOT match up perfectly to the pre-fabricated custom craniofacial implant (versus as originally envisioned, for example, as designed in a planning stage). Or in a scenario where normal bone is to be removed simply to assure proper contour with neuromodulation implantation, one could use a pre-fabricated cutting guide for custom cranial implant placement.

Due to the recent reductions for time needed to design, fabricate and implant custom craniofacial implants, more cranioplasty procedures with alloplastic implants are being performed around the world than ever before. Accordingly, these recent developments in custom craniofacial implant sterility, shape design, and streamline production-together provide an opportunity that extends custom craniofacial implant-based cranioplasty beyond only patients who require replacement of pre-existing craniectomy defects.

SUMMARY OF THE INVENTION

The present invention advances the possibilities associ-ated with custom craniofacial implants by providing pre-fabricated, customized, patient-specific implantable devices with low-profiles (i.e., to avoid unnecessary contour irregu-larities, scalp-related complications, and high extrusion risk leading to premature explantation). The present invention also provides methods of making and implanting such implant devices, including methods using computer-assisted surgical procedures, such as computer-assisted cranioplasty (see PCT Publication No. WO 2016/086054, based upon PCT Application No. PCT/US2015/062521, entitled "COMPUTER ASSISTED CRANIOPLASTY," which is incorporated herein by reference) and/or robot-assisted implant modification (see PCT Publication No. WO 2016/086049, based upon PCT Application No. PCT/US2015/062516, entitled "A CUTTING MACHINE FOR RESIZING RAW IMPLANTS DURING SURGERY," which is incorporated herein by reference).

Still further, the present invention optimizes the relationship between custom craniofacial implants and functional neurological implants in synergy-making it possible to integrate these "normally asymmetric" components within a low-profile intercranial device for provision of enhanced treatment to patients. Such improvements exploit the benefits of direct access to the brain and ideal anatomical location/proximity provided by these novel custom craniofacial implants placed directly on top and just a few millimeters away from the brain to deliver life-changing interventions providing an unprecedented method to deliver locally, for example, Neurologic Deep Brain stimulations, or neurologic medicines, that are otherwise prevented from diffusing through the blood-brain barrier via common delivery methods (i.e., oral, intravenous) and battery-powered functions via various encased components including neuromodulation devices, imaging devices, radiation therapy devices, and remote sensing/monitoring devices.

It is, therefore, an object of the present invention to provide a low-profile intercranial device including a low-profile static cranial implant and a functional neurosurgical implant, wherein the low-profile static cranial implant and the functional neurosurgical implant are designed and interdigitated prior to physical assembly of the low-profile intercranial device.

It is also an object of the present invention to provide a method for manufacturing a low-profile intercranial device including virtual design and interdigitating of distinct cranial implants prior to physical manufacture of the low-profile intercranial device. The method includes creating a static cranial implant, creating a functional neurosurgical implant shaped and dimensioned to interdigitate with the static cranial implant, and integrating the functional neurosurgical implant with the static cranial implant.

It is a further object of the present invention to provide a method for the implantation of a low-profile intercranial device including a static cranial implant and a functional neurosurgical implant positioned within a cavity of the static cranial implant. The method includes diagnosing a need for implantation of the low profile intercranial device as a replacement for a specific portion of a cranium of a patient, creating the static cranial implant, creating the functional neurosurgical implant, integrating the functional neurosurgical implant with the static cranial implant, and implanting the low-profile intercranial device within the intercranial space.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 13 is a perspective view of a low-profile intercranial device including a customized static cranial implant with alignment lines in accordance with an alternate embodiment of the present invention.

FIG. 14 is a perspective view of a low-profile intercranial device including a customized static cranial implant with relief recesses in accordance with an alternate embodiment of the present invention.

FIG. 15 is a perspective view of a low-profile intercranial device including a customized static cranial implant with laser cuts and laser markings in accordance with an alternate embodiment of the present invention.

FIG. 22 is a perspective view of a low-profile intercranial device in accordance with an alternate embodiment wherein the customized static cranial implant is of a two-piece construction and the functional neurosurgical implant is a remote video unit.

FIGS. 23, 24 and 25 are respectively perspective views of different embodiments showing the low profile intercranial device with a functional neurosurgical implant in the form of a deep brain stimulation device, a shunt device and a brain mapping device.

5

6

Figures 1, 2:
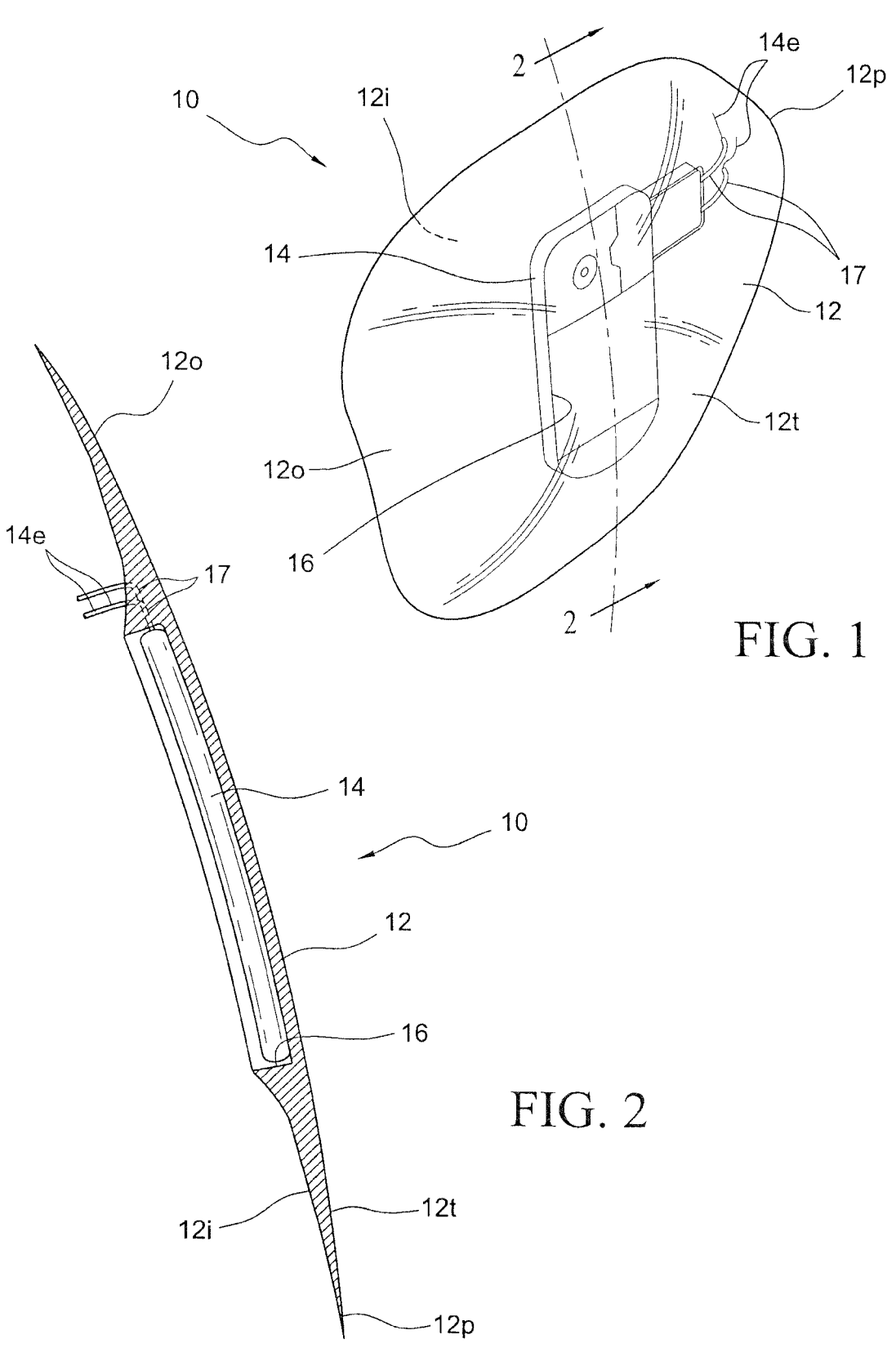
FIG. 1 is a perspective view of a low-profile intercranial device in accordance with a preferred embodiment of the present invention.
FIG. 2 is a sectional view of the low-profile intercranial device shown in FIG. 1.

FIG. 26 is a perspective view of a 3-D printer that may be used in accordance with the present invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention. For example, while the disclosure is preferably directed to a low-profile intercranial device that includes a customized cranial implant, it is within the scope of the disclosure that the cranial implant could be fabricated and provided as a standardized shape or size implant configured to receive a standard size and shape functional implant, rather than a patient-specific customized implant designed to conform to the skull opening. This is especially the case where skull resection is not determined, for example, by the shape of a resected tumor and may be created in a standardized manner specifically to accommodate the low-profile intercranial device of the present disclosure.

As used within this disclosure, the term "intercranial" means situated or occurring within the cranium itself such that such devices are positioned within the space existing between the inner surface of the scalp and the outer surface of the dura. As such, intercranial devices are those devices intended for positioning within the cranium itself as opposed to devices that may be positioned on or adjacent to the cranium or positioned along the interior of the cranium, for example, between the cerebral cortex and the interior surface of the cranium. With this in mind, intercranial devices such as those discussed below replace resected portions of the cranium due to abnormalities in the cranium, damage to the cranium, or other medically sufficient reasons for resecting positions of the cranium.

With reference to the various figures, a low-profile intercranial device 10 and a method for manufacturing the low-profile intercranial device 10 are disclosed. In addition to the actual manufacture of the low-profile intercranial device 10, the present method includes the virtual design and maximal interdigitating of distinct cranial implants (that is, a low-profile customized static cranial implant 12 and a functional neurosurgical implant 14 in accordance with a preferred embodiment of the present invention) prior to the physical manufacture of the low-profile intercranial device 10. The term "interdigitating" is meant to refer to the interlocking of two distinct elements (that is, the low-profile customized static cranial implant 12 and a functional neurosurgical implant 14) such that the two distinct elements mesh together to ultimately define a single product. It is appreciated that while the various embodiments disclosed herein only show a single functional neurosurgical implant in conjunction with a low-profile customized static cranial implant, multiple functional neurosurgical implants may be used in a single low-profile intercranial device in accordance with the present invention As mentioned above, the low-profile intercranial device 10 is generally composed of a customized static cranial implant 12 and an interdigitating functional neurosurgical implant 14. This combination of elements results in the present low-profile intercranial device 10 that improves and optimizes the spatial arrangement between the customized static cranial implant 12 and the functional neurosurgical implant 14 when placed within the confines of one's skull (as opposed to the current methods where functional neurosurgical implants are positioned "above" or "below" the skull). The low-profile intercranial device 10 is particularly adapted for ideal functional and aesthetic benefits, thereby minimizing unnecessary spaces, inter-implant gaps, and sharp irregular angles. This helps to minimize risk of scalp pain, visible deformity, and implant micromotion-all of which often leads to treatment failure and surgical explantation (that is, premature removal of the implant).

More specifically, the low-profile intercranial device 10 of the present invention employs a CT (Computed Tomography) scan-based, virtual design session performed pre-operatively based on the brain-specific geographical location (as opposed to the standard method of using the skull-specific geographic location). As a result, and for the first time, the methodology employed in accordance with the present invention accommodates both brain and skull pathology in three-dimensional space, in all three axes, prior to surgery unlike ever before.

With this information, as well as knowledge regarding the dimensions of the functional neurosurgical implant 14, the customized static cranial implant 12 is produced. The customized static cranial implant 12 is augmented, reduced and/or modified to include a hollowed-out center cavity 16 (it is appreciated multiple cavities may be employed where the functional neurosurgical implant(s) being used dictates and that the cavity need not be directly in the center of the customized static cranial implant 12 but may be offset as dictated by the procedure being performed), as well as other structural elements 17 (for example, wire tunnel(s), pocket (s), etc.), shaped and dimensioned for optimal anatomical placement of the functional neurosurgical implant 14 that is ultimately positioned within the confines of the center cavity 16 (and other structural elements 17) of the customized static cranial implant 12 (i.e., like an empty shell case but with exact negative and positive enhancements to optimize anatomical positioning of both the customized static cranial implant 12 and the functional neurosurgical implant 14). Depending upon the specifics of the functional neurosurgical implant 14 positioned within the center cavity 16 of the of customized static cranial implant 12, various mechanical coupling mechanisms, for example, screws, plates, etc. (not shown), are used to ensure that the functional neurosurgical implant 14 is securely held in place. As will be explained below in greater detail, the manufacture of the low-profile intercranial device 10 utilizes computer-based designs of both the customized static cranial implant 12 and the functional neurosurgical implant 14.

The computer-based designs of the customized static cranial implant 12 and the functional neurosurgical implant 14 are optimized during virtual design sessions incorporating neurosurgeon, plastic-reconstructive, or other surgeon input. The optimization process takes into account the three-dimensional, spatial relationship between the customized static cranial implant 12 and the functional neurosurgical implant 14 (amongst one another if there is more than one functional neurosurgical implant), as well as the underlying topographical relationship of the customized static cranial implant 12/functional neurosurgical implant 14 with the brain-skull anatomy and physiology of the specific patient for whom the low-profile intercranial device 10 is being customized and manufactured. Modification of a digitally rendered base static cranial implant 112a with a final shape and contour before sterilization and surgical implantation in accordance with the present invention (to produce the final customized static cranial implant 12)

results in the present low-profile intercranial device 10. Through this process the spatial arrangement between the low-profile customized static cranial implant 12 and the functional neurosurgical implant 14 is improved when placed within the confines of one's skull. This represents a major advancement in the field of neurosurgery and plastic-reconstructive surgery versus current methods, which involve placing the functional neurosurgical implant either "above" or "below" the skull, are not patient-specific, and are not using a cranial implant as a protective covering.

The term "static" is used in the description of the present invention because the customized static cranial implant 12, has no encapsulated inner working (i.e., "functional") parts, batteries, wires, or computers, and is essentially an improved "empty-shell" which optimizes the inter-implant positioning within the confines of the skull and the neighboring functional neurosurgical implant 14.

Briefly, and as will be appreciated based upon the following disclosure, the customized static cranial implant 12 of the present invention is a modified version of a low-profile cranial implant commonly used and known by those skilled in the art of cranial surgical procedures. Such implants may take a variety of forms and are most commonly shaped and dimensioned for integration into the structure of a patient's skull; that is, the customized cranial implant has a geometry that substantially conforms with a resected portion of the patient's anatomy to which the implant is to be secured. Briefly, the customized static cranial implant 12 of the present invention includes an outer (commonly convex) first surface 120, an inner (commonly concave) second surface 12i, and a peripheral edge 12p extending between the outer first surface 120 and the inner second surface 12i. The customized static cranial implant 12 is shaped and dimensioned for engagement with the skull of the patient upon implantation in a manner well known to those skilled in the field of neurosurgical procedures. The outer first surface 120 and inner second surface 12i of the customized static cranial implant 12 are preferably curved in a superior to inferior direction, a posterior to anterior direction, and a medial to lateral direction. In addition, and as noted in the embodiments discussed with reference to FIGS. 2, 10, and 17, the peripheral edge 12p has a substantial taper for resting upon a matching taper formed along the skull. It is, however, appreciated that this taper may vary (or not exist at all, that is, the peripheral edge may be substantially perpendicular relative to the outer first surface and the inner second surface) depending upon the specific needs of the procedure. In accordance with a preferred embodiment, the customized static cranial implant will have a preselected thickness not exceeding the space between the inner surface of the scalp and the outer surface of the dura, for example, in the range of around 1 millimeter to 25 millimeters (with areas of strategic bulking and/or thinning) and depending upon the strength of the materials used in the construction of the customized static cranial implant 12. Preferably, the customized static cranial implant 12 will have a thickness of 1 millimeter to 12 millimeters.

As mentioned above, the customized static cranial implant 12 also includes a cavity 16 (for example, formed along the inner surface) and optional structural elements 17, for example, channels, pockets, access holes, and/or other structural elements, designed to accommodate various features of the functional neurosurgical implant 14. In the disclosed embodiment, structural elements in the form of channels 17 are provided. The channels 17 have a first end in communication with the center cavity 16 and a second end extending to the inner second surface 12i (or top surface 12t)

of the customized static cranial implant 12 for the passage of electrodes 14e of the functional neurosurgical implant 14 for applying stimulation to the brain. As many functional neurosurgical implants 14 such as disclosed in FIGS. 1, 2, 10, 11 and 13-17 interact with a control device (not shown) via wireless mechanisms, access between the outer first surface 120 (or top surface 12t) and the center cavity 16 may not be required, although it is appreciated channels or other structural elements could certainly be provided for external contact as needed and as shown in the embodiment disclosed with reference to the deep brain stimulation device 320 shown in FIG. 23.

In accordance with a preferred embodiment, the customized cranial implant 12 is fabricated from a wide array of commonly-available biomaterials including, but not limited to, clear and/or opaque PMMA (Poly(methyl methacrylate)), PEEK (Polyether ether ketone), PEKK (Polyetherketoneketone), porous polyethylene, titanium alloy, allograft, autograft, xenograft, and/or various other tissue-engineered constructs. In accordance with one embodiment, the customized static cranial implant 12 is ideally made of clear PMMA since it's fully radiolucent and transparent. This allows for novel inspection of the interdigitated functional neurosurgical implant 14 and neighboring components. As will be explained below in greater detail, it also allows for the critical transmission of vital imaging with minimal distortion, such as ultrasound waves for brain pathology detection, radio-frequency (RF) transmission, and wireless signal communication (i.e., electroencephalography or ECOG)—essential for various neuromodulation devices such as NeuroPace®, for example. Another clear material that may be readily used in accordance with the present invention is cubic zirconium. While clear material is disclosed in accordance with a preferred embodiment, it is appreciated the underlying concepts of the present invention may be achieved through the utilization of an opaque customized static cranial implant 12 as shown with reference to FIG. 9.

The optical clarity of the customized static cranial implant 12 is important in expanding the potential uses of the low-profile intercranial device 10 and in expanding the potential functional neurosurgical implants 14 that may be used in conjunction with the present invention. For example, the provision of high optical clarity allows for wireless optical links between the functional neurosurgical implants 14 and remote devices or between functional devices on the interior of the cranium and the exterior of the low-profile intercranial device 10 (for example, transmitting between the cortex and the other side of the low-profile intercranial device 10). Enhanced optical clarity similarly allows for power transmission and/or receipt between the functional neurosurgical implants 14 and devices outside of the customized static cranial implant 12. Potential operations that may be achieved through the utilization of optical links through a high clarity customized static cranial implant 12 include, but are not limited to, device start-up, device calibration, and device operational control.

Still further, the customized static cranial implant 12 is constructed of a material allowing for imaging of the brain through the customized static cranial implant 12, for example, via ultra-sound. It is known that clear PMMA will provide the ability to permit ultra-sound imaging of the brain therethrough so long as it is manufactured without additives that might function to block the radio waves of the imaging device. In addition, and with reference to FIG. 10, the customized static cranial implant 12 may include an embedded antibiotic (shown as little dots 13), which is mixed with the polymer from which the customized static cranial implant 12 is made, to help reduce the risk of acute or chronic infections from occurring.

Figures 9, 10, 11, 12:
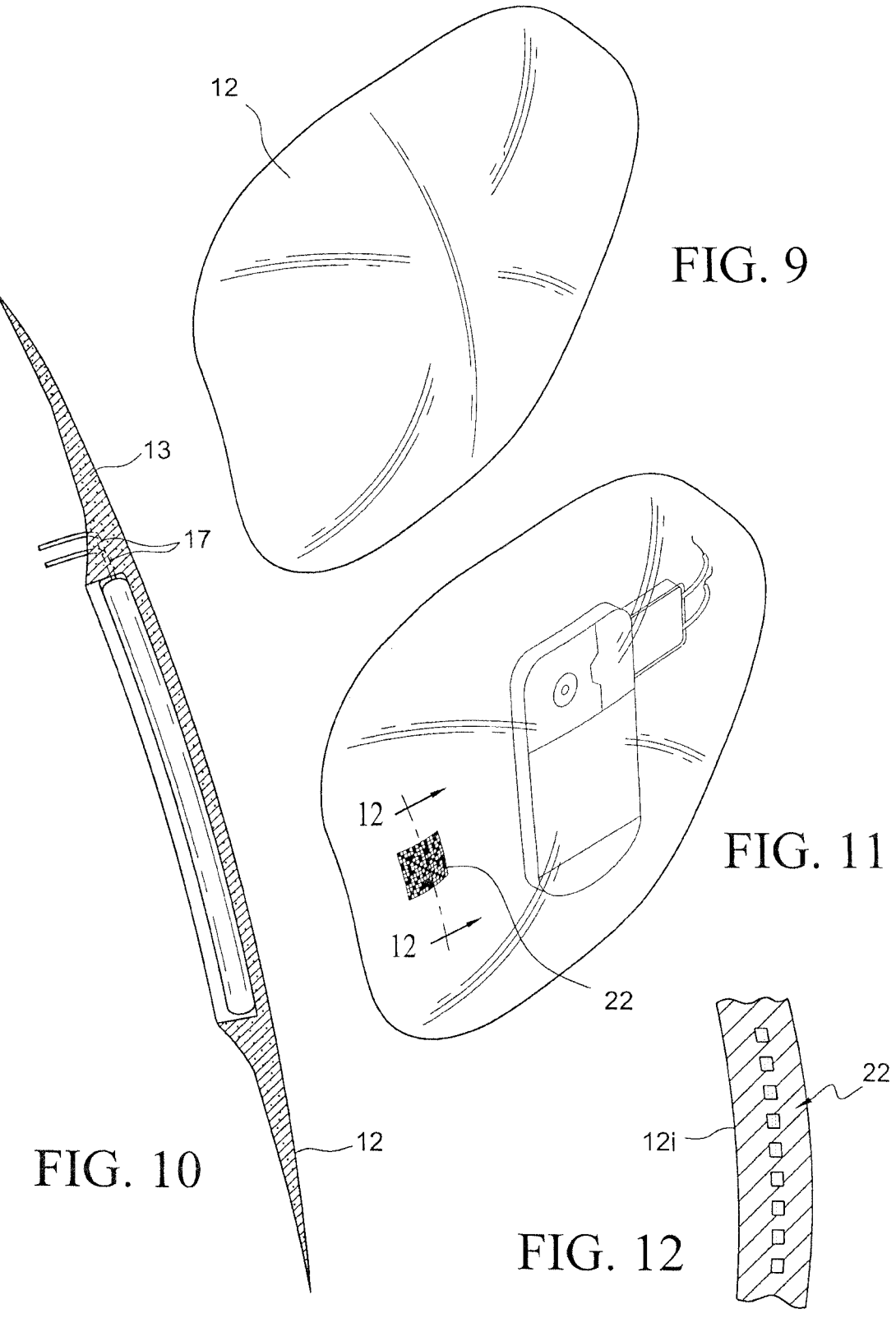
FIG. 9 is a perspective view of an opaque customized static cranial implant in accordance with an alternate embodiment of the present invention.
FIG. 10 is a cross sectional view of a low-profile intercranial device showing a customized static cranial implant fabricated with embedded antibiotics in accordance with an alternate embodiment of the present invention.
FIG. 11 is a perspective view of a low-profile intercranial device including a customized static cranial implant with an embedded serial number in accordance with an alternate embodiment of the present invention.
FIG. 12 is a cross sectional view along the line 12-12 in FIG. 11.

With reference to FIGS. 11 and 12, the customized static cranial implant 12 may also be provided with an embedded serial number (or implant identifier) 22 that is viewable via CT or MRI (Magnetic Resonance Imaging) scan. In accordance with a preferred embodiment, such embedded serial numbers 22 will be positioned along the inner second surface 12i of the customized static cranial implant 12. The embedded serial number 22 is preferably in the form of a QR (Quick Response) Code, that is, a two dimensional barcode offering enhanced patient privacy, ready readability, and vast versatility. The embedded serial number 22 is achieved by integrating various materials that are viewable via CT or MRI scan into the base material of the customized static cranial implant 12. For example, the materials may be barium sulfate or zirconium dioxide integrated into the customized static cranial implant so as to function as a serial number that may be viewed after implant.

As shown with reference to FIG. 13, the customized static cranial implant 12 is also preferably constructed with alignment markings 24, 26. In accordance with a preferred embodiment, the alignment markings 24, 26 run fully across the customized static cranial implant 12 and are formed in the shape of a cross. As such, the alignment markings 24, 26 include a first alignment marking 24 formed upon the customized static cranial implant 12 to identify the superior to the inferior direction of the low-profile intercranial device 10 when properly implanted, and a second alignment marking 26 formed upon the customized static cranial implant 12 necessary to identify the posterior to anterior direction of the low-profile intercranial device 10 when properly implanted. These alignment markings 24, 26 are preferably formed via laser etching of the customized static cranial implant as the customized static cranial implant is fabricated for use in accordance with the present invention. The laser etching may be combined with CNC (Computer Numerically Controlled) techniques to optimize the accuracy of markings or other known marking techniques may be employed were they offer sufficient accuracy to warrant use in accordance with the present invention.

The customized static cranial implant 12 of the present invention may be provided with relief recesses 30 (see FIG. 14) for the creation of a perfectly smooth surface when titanium plates are utilized in conjunction with the low-profile intercranial device 10 for securing the low-profile intercranial device 10 in a desired position. In accordance with such an embodiment, the relief recesses 30 are 0.4 mm in depth as titanium plates are known to be very thin.

Still further, and with reference to FIG. 15, the customize static cranial implant 12 may be provided with laser cut lines 32 identifying cuts for various other devices that may be utilized in conjunction with the low-profile intercranial device 10. For example, the laser cut lines 32 might identify the location of a NeuroPace® neurostimulator device positioned adjacent to the low-profile intercranial device 10. Still further, the laser cut lines 32 may be utilized for providing insight into the desired location of the low-profile intercranial device 10.

In addition to laser cut lines 32, laser markings 34 maybe made along the outer first surface 120 or inner second surface 12i of the customized static cranial implant 12 to provide an indication of critical anatomy relating to the installation of the low-profile intercranial device 10 in accordance with the present invention. For example, such laser markings 34 might be useful in identifying critical neuro anatomy relating to the functional neurosurgical implant 14 of the low-profile intercranial device 10.

While a preferred customized static cranial implant 12 is disclosed in accordance with the present invention, the customized static cranial implant 12 used in conjunction with the present invention may take a variety of forms so long as the customized static cranial implant 12 includes a center cavity 16 (and, optionally, other structural elements 17) configured to conform to the exact requirements of the functional neurosurgical implant 14 in accordance with the present invention.

While a one-piece construction for the customized static cranial implant 12 is disclosed above, multiple-piece constructions are contemplated in accordance with the present invention. For example, and with reference to FIGS. 18-22, 24 and 25, the customized static cranial implant 212 may have a two-piece construction allowing for ready access to the functional neurosurgical implant 14 without the need for complete removal of the low-profile intercranial device 210. As with the embodiment described above, the two-piece customized static cranial implant 212 has no encapsulated inner working parts, batteries, wires, or computers, and is essentially an improved "empty-shell."

The two-piece customized static cranial implant 212 in accordance with this embodiment includes a base cranial implant member 214 and a cover cranial implant member 215. The base cranial implant member 214 has a geometry that substantially conforms with a resected portion of the patient's anatomy to which the low-profile intercranial device 210 is to be secured. The base cranial implant member 214 includes an outer (commonly convex) first surface 2140, an inner (commonly concave) second surface 214i, and a peripheral edge 214p extending between the outer first surface 2140 and the inner second surface 214i. The customized static cranial implant 212 is shaped and dimensioned for engagement with the skull of the patient upon implantation in a manner well known to those skilled in the field of neurosurgical procedures. The outer first surface 2140 and inner second surface 214i of the base cranial implant member 214 are preferably curved in a superior to inferior direction, a posterior to anterior direction, and a medial to lateral direction.

The base cranial implant member 214 also includes a center recess 216 formed along the outer first surface 2140 and optional structural elements 217, for example, channels, pockets, access holes, and/or other structural elements, designed to accommodate various features of the functional neurosurgical implant 14. As with the prior embodiment, multiple recesses may be employed where the functional neurosurgical implant(s) being used dictates and that the recess need not be directly in the center of the base cranial implant member but may be offset as dictated by the procedure being performed.

In accordance with a preferred embodiment, the base cranial implant member 214 is fabricated from a wide array of commonly-available biomaterials including, but not limited to, clear and/or opaque PMMA (Poly(methyl methacrylate)), PEEK (Polyether ether ketone), PEKK (Polyetherketoneketone), porous polyethylene, titanium alloy, and/or various other tissue-engineered constructs. In accordance with one embodiment, the base cranial implant member 214 is ideally made of a clear PMMA since it's completely transparent and fully lucent. This allows for novel inspection of the interdigitated functional neurosurgical implant 14 and neighboring components.

In addition to the base cranial implant member 214, the two-piece customized static cranial implant 212 includes a cover cranial implant member 215. The cover cranial implant member 215 is shaped and dimensioned for positioning over the center recess 216 along the outer first surface 2140 of the base cranial implant member 214. In accordance with a preferred embodiment, the cover cranial implant member 215 is secured to the base cranial implant member 214 by screw fixation 219. The cover cranial implant member 215 includes an outer (commonly convex) first surface 2150, an inner (commonly concave) second surface 215i, and a peripheral edge 215p shaped and dimensioned for engagement with the outer first surface 2140 of the base cranial implant member 214 along the periphery of the center recess 216. As with the base cranial implant member 214, the outer first surface 2150 and inner second surface 215i of the cover cranial implant member 215 are preferably curved in a superior to inferior direction, a posterior to anterior direction, and a medial to lateral direction.

The base cranial implant member 214 and the cover cranial implant member 215 have a total thickness similar to that of the embodiment described above, that is, and depending on the strength characteristics of the materials used, the base cranial implant member 214 and the cover cranial implant member 215 will have a thickness (with areas of strategic bulking and/or thinning) of around 1 millimeter to 25 millimeters, preferably, 1 millimeter to 12 millimeters.

As mentioned above, the cover cranial implant member 215 fits over the center recess 216 along the outer first surface 2140 of the base cranial implant member 214. In this way, the inner second surface 215i of the cover cranial implant member 215 and the outer first surface 2140 of the base cranial implant member 214, along the center recess 216, define a center cavity 220 configured to conform to the exact requirements of the functional neurosurgical implant 14 in accordance with the present invention. With this in mind, the inner second surface 215i of the cover cranial implant member 215 may be shaped and/or contoured to enhance the positioning of the functional neurosurgical implant 14 within the center cavity 220.

The functional neurosurgical implant 14 of the present invention is selected from a variety of FDA-approved and experimental options for electrical, optical, mechanical, medicinal and other treatment/monitoring devices designed for long term invasive treatment and/or disease-monitoring of patients requiring such attention. These functional neurosurgical implants 14 are known devices manufactured by various vendors within the neurosurgical industry and have known, unmodifiable dimensions that may be used in the modification of the customized static cranial implant 12 to optimize surgical results by minimizing abnormal shapes, visible contours, and/or craniofacial deformities.

Based upon the functional neurosurgical implant 14 used in conjunction with the present invention, the functional neurosurgical implant 14 may be useful in the treatment of various patient conditions such as epilepsy, movement disorders, chronic pain, spasticity, cerebral palsy, multiple sclerosis, spinal cord injury, traumatic brain injury, attention-deficit/hyperactivity disorder, autism, etc.—and the potential to obtain supra-normal levels of brain function in both military and civilian situations. Furthermore, incorporation of imaging devices within cranial implants could help to provide ongoing tumor bed monitoring for early detection of disease recurrence.

By way of example, one potential functional neurosurgical implant 14 that may be employed in accordance with the present invention is a battery powered functional neurosurgical implant with "radio-frequency (RF) functionality known as the NeuroPace® device, that is, a device for responsive neurostimulation for epilepsy, which has a design flaw in that it limits the visible aesthetic result due to its irregular shape(s), requires placement of battery(es) within the chest with wires going along the neck, and suffers from high rates of implant micromotion thereby leading to common device infection and bone flap osteomyelitis (See, Wei Z, Gordon C R, Bergey G K, Sacks J M, Anderson W S. Implant Site Infection and Bone Flap Osteomyelitis Associated with the NeuroPace Responsive Neurostimulation System. World Neurosurg 2015 Dec. 29; pii: s1878-8750 (15)01775-1.) These deficiencies are overcome in accordance with the present invention by optimizing the customized static cranial implant 12 for receipt of the NeuroPace® device."

Further, the present invention allows the possibility of combining the benefits of the ideal contour customized static cranial implant 12 with the efficacy of neuromodulation potentially reducing the complication rates of repetitive nerve stimulation (RNS) to the complication rates of cranial reconstruction (50% to 3-4%) and giving surgeons an option when the existing bone is resorbing.

The present invention also allows the possibility of combining the benefits of the present low-pressure intercranial device 10 with the ability to monitor cranial pressure mitigating the needs for excessive imaging, offering patients and surgeons the ability to capture spikes or drops in pressure related to hydrocephalous, hematoma, stroke, etc.

The present invention also allows the possibility of combining the benefits of the present low-pressure intercranial device 10 with the ability to control hydrocephalous or overactive ventricles possibly preventing a second surgical sight for shunt placement and at least eliminate the irregular contour and work time of post fabrication modification of cranial reconstruction implant.

The present invention also allows the possibility of reducing or eliminating the need for post-operative imaging, saving money for insurance companies, providing peace of mind for patients, and allowing on-demand assessment for surgeons.

The present invention also allows the possibility of combining the benefits of the present customized static cranial implant with the ability to deliver pharmaceuticals past the blood brain barrier. The proximity to the ventricles or excised tumor beds reduces the clinical challenges of tunneling catheters great distances from other anatomies.

Another functional neurosurgical implant 14 that may be used in conjunction with the customized static low-pressure intercranial device 210 is a remote video unit 314 (see FIG. 22). Considering the fact the customized static cranial implant 212 is clear, a remote video unit 314 may be deployed for viewing the brain and in particular the healing of the brain in the area adjacent to the low-profile intercranial device 210. Where the two-piece customized static cranial implant 212 is employed, the remote video unit 314 could be selectively removed and deployed by simply accessing the cover cranial implant member 215 and removing the same allowing for access to or deployment of the remote video unit 314. In addition to batteries, lenses and other components commonly employed in conjunction with digital cameras, the remote video unit 314 includes a Bluetooth transmitter 316 allowing for the transmission of images to a remote display where the images may be viewed or stored for later viewing. Still further, and with reference to FIGS. 23, 24 and 25, functional neurosurgical implants 14 that may be used in conjunction with the low-profile intercranial device 210 include a deep brain stimulation device 320 (FIG. 23), a shunt device 330 (FIG. 24) and a brain mapping device 340 (FIG. 25).

With the foregoing in mind, additional functional neurosurgical implants 14 that may be used in conjunction with the present invention include, but are not limited to the following: Deep Brain Stimulators (DBS); Cortical Brain Stimulators (CBS); neurologic medicines that are otherwise prevented from diffusing through the blood-brain barrier via common delivery methods; battery/passively/kinetically/or otherwise-powered functional devices including neuromodulation devices, imaging devices, radiation therapy devices, and remote sensing/monitoring devices; monitoring devices for abnormal levels of intracranial pressure (ICP) or brain activity (i.e., seizures), such as an electrical array for motor/vision cortex control, battery/passively/kinetically/or otherwise-based stimulation hardware for epilepsy management (grids/batteries/wires); low-profile remote imaging devices (e.g., optical coherence tomography (OCT), duplex ultrasound); delivery/sensing devices for electrical impulses; neurological and physiological systems required for deep space/sleep functionalities enhancing the monitoring and/or maintenance of bodily vital signs, nutrition, cognition, etc.; convection enhanced delivery systems effectively delivering therapeutics to substantial volumes of brain and brain tumor; and remote neuro-imaging devices (i.e., electroencephalogram (EEG).

The functional neurosurgical implants 14 of the present invention may also incorporate high-precision and fully implantable next-generation neural interface systems taking advantage of microelectronics and photonics along with advances in scalable neural encoding and processing algorithms to demonstrate the transformation of high-definition sensory stimuli to and from sensory cortex areas, bridging physiological and electronic neural activity representations.

With this in mind, the term "functional neurosurgical implant" is meant to reference any therapeutic hardware or compositions including, but not limited to, medicines to treat any patient-specific illness, or electronic, mechanical, imaging modality and/or electro-mechanical device to remotely monitor (e.g., via Wi-Fi connectivity) or intervene any specific neurologic illness, including imaging, monitoring, electrostimulation, radiation therapy, polarized light/laser neuronal modulation devices. The term "functional" denotes the fact that these implants provide the low-profile intercranial device 10 with the ability to function as more than a safe custom-shaped skull replacement by providing various functionalities, for example, local drug delivery, monitoring (such as brain monitoring), or local electric stimulation to the patient.

Figure 3:
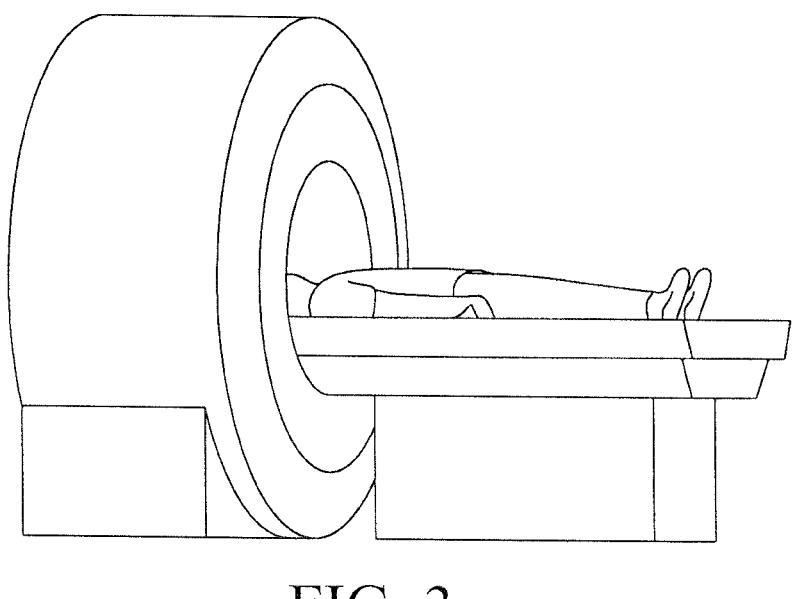
FIG. 3 shows a patient obtaining protocol CT scan prior to surgery.

The following describes the steps employed in the manufacture and installation of the low-profile intercranial device 10 of the present invention. While the procedure is described for manufacture and installation of the one-piece customized static cranial implant, the two-piece customized static cranial implant is processed in the same manner. After the patient is diagnosed as requiring the implantation of a low profile intercranial device 10 as a replacement for a specific portion of the cranium (either to reconstruct a portion of the cranium or to replace a surgeon created defect) in accordance with the claimed invention, the patient first undergoes a high-definition, protocol CT scan of his or her head prior to surgery (which is customary for all neurosurgical patients in need of cranial implants) (see FIG. 3) and the CT scan is then converted to an STL file (or other digital data format useful in computer-assisted design/computer-assisted manufacture (CAD/CAM) manufacture procedures) (see FIG. 4).

Figure 4:
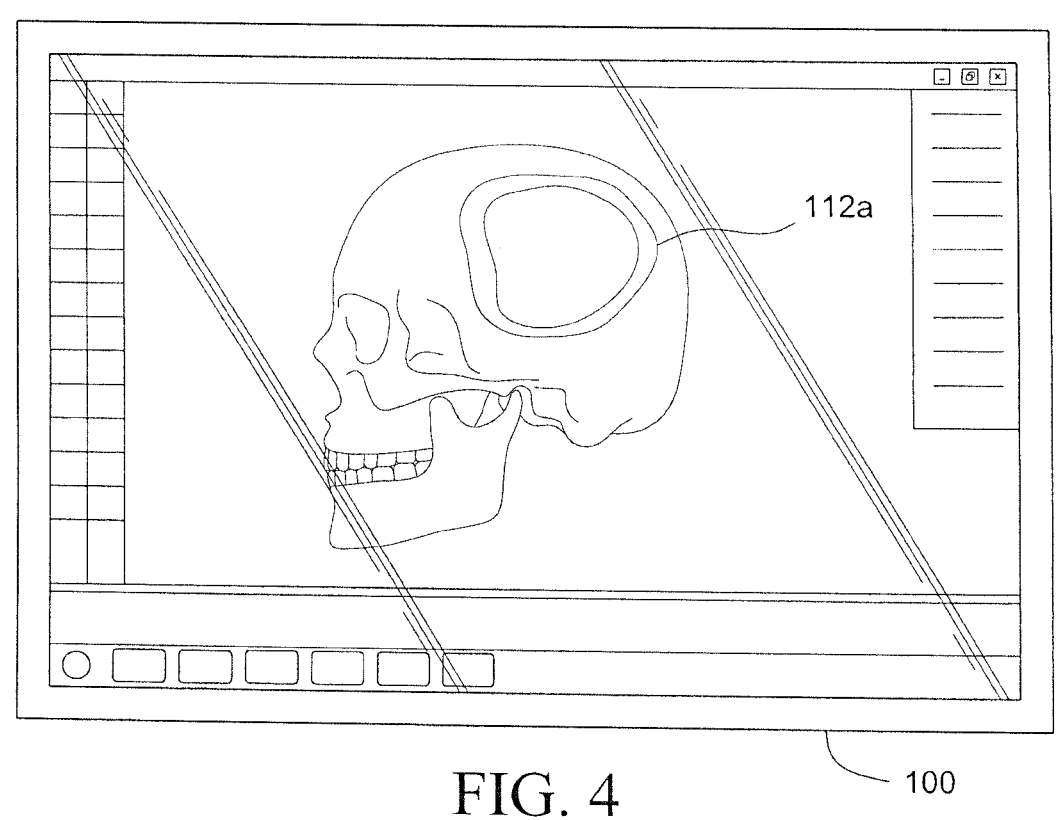
FIG. 4 shows the CT scan is then converted to a digital data format useful in computer-assisted design/computer-assisted manufacture (CAD/CAM) manufacture procedures.
Figures 5, 6:
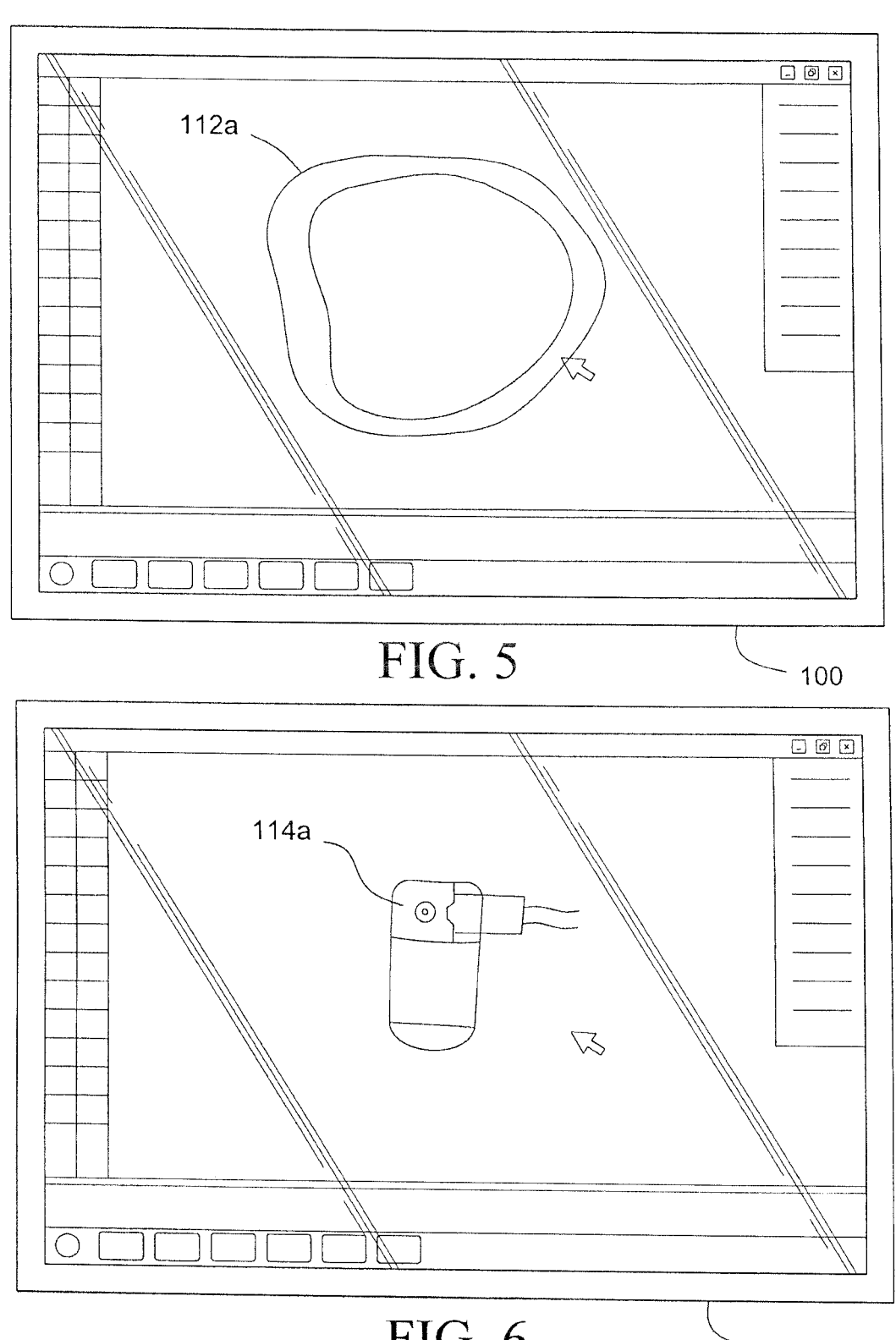
FIG. 5 is a computer screenshot showing a digitally rendered base static cranial implant in accordance with the present invention.
FIG. 6 is a computer screenshot showing a digitally rendered functional neurosurgical implant in accordance with the present invention.

With the STL file of the CT scan completed, the digital image of the patient (for those patients either with or without an existing skull defect) is used by a design engineer to create a digitally rendered base static cranial implant 112a using conventional computer-assisted design (CAD)/computer-assisted modeling (CAM) techniques (See FIGS. 4 and 5). Feedback from a surgeon(s) pre-operatively helps to reveal any unexpected surgical details and aids one in confirming an ideal, planned location of functional neurosurgery and relevant topographical brain anatomy underneath the planned low-profile intercranial device 10. It is appreciated the CAD/CAM techniques, as well as other automated elements of the present methodology are accomplished using conventional computer and technology equipment 100 well known to those skilled in the art. The digitally rendered base static cranial implant 112a exhibits a shape exact to the size, thickness, and contour of the patient's unique cranium. The digitally rendered base static cranial implant 112a is then stored as an STL file (or other digital data format useful in computer-assisted design manufacture procedures).

Simultaneously, before or after the creation of the digital design of the cranial implant, a digital rendering of the functional neurosurgical implant ("digitally rendered functional neurosurgical implant 114a") to be used with the customized static cranial implant 12 is created (or obtained from the third party vendor responsible for the manufacture of the functional neurosurgical implant (See FIG. 6). As with the digitally rendered base static cranial implant 112a, the digitally rendered functional neurosurgical implant 114a is stored as an STL file (or other digital data format useful in computer-assisted design manufacture procedures) commonly used by design engineers using (CAD)/(CAM) techniques and, as explained below, the exact dimensions of the functional neurosurgical implant are incorporated into the final low-profile intercranial device 10 of the present invention.

Figure 7:
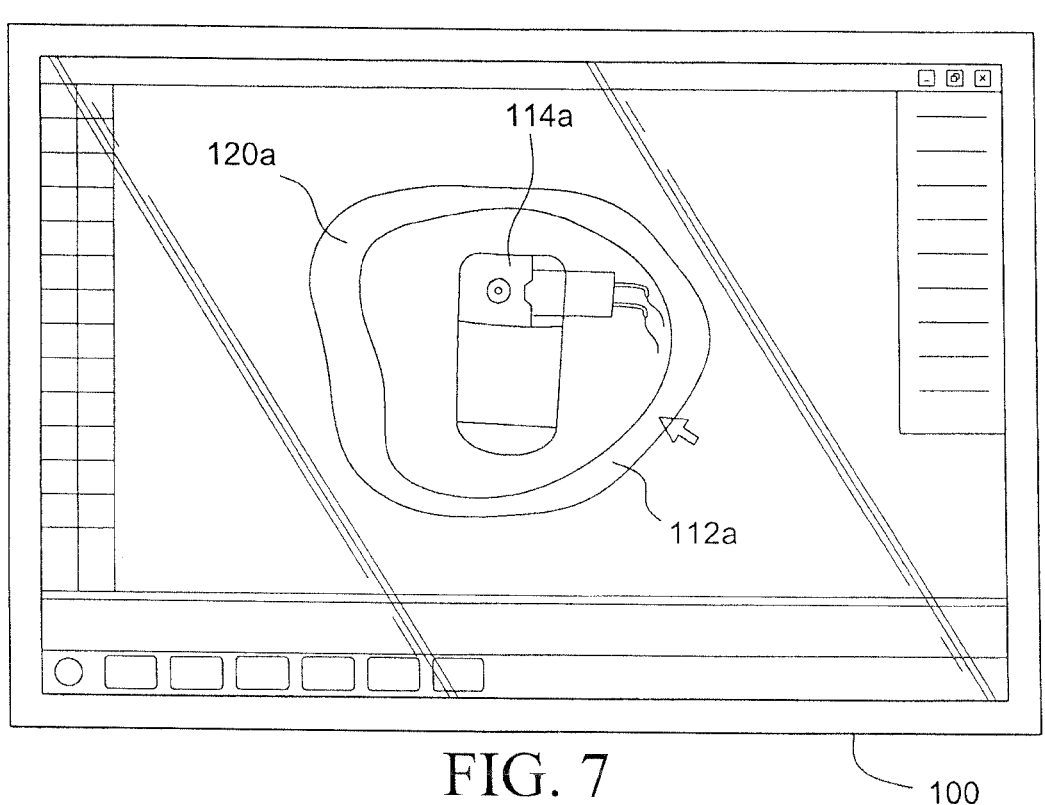
FIG. 7 is a computer screenshot showing a hybrid rendering in accordance with the present invention.

The digitally rendered functional neurosurgical implant 114a is then superimposed on the digitally rendered base static cranial implant 112a to produce a hybrid rendering 120a including both the digitally rendered functional neurosurgical implant 114a and the digitally rendered base static cranial implant 112a (see FIG. 7). It is appreciated multiple digital renderings of functional neurosurgical implants will be created and superimposed where the planned low-profile intercranial device 10 includes multiple functional neurosurgical implants. With the digitally rendered functional neurosurgical implant 114a superimposed on the digitally rendered base static cranial implant 112a as a single superimposed digital drawing (that is, the hybrid rendering 120a), the functional neurosurgical implant and the cranial implant (that is, the digitally rendered versions of both) may be optimized with patient-specific independent width/height/length dimensions to optimize anatomical harmony amongst the functional neurosurgical implant 14 and the customized static cranial implant 12 prior to surgery and allow virtual planning for the seamless integration of the functional neurosurgical implant 14 and the customized static cranial implant 12. This optimization process results in the optimized hybrid rendering 120b, composed of an optimized digitally rendered functional neurosurgical implant 114b and the optimized digitally rendered customized static cranial implant 112b as shown in FIG. 8.

In particular, and with the digitally rendered functional neurosurgical implant 114a superimposed on the digitally rendered base static cranial implant 112a, the center cavity, that is, the digitally rendered center cavity 116b (as well as linear channels for wires to tunnel through, pockets to pack excess wire length, access holes for battery replacement, etc.—referenced as structural element 117*b*) of the customized static cranial implant 12 are designed and integrated into the optimized hybrid rendering 120*b*. The digitally rendered center cavity 116*b* (and other structural elements 117*b*) is designed virtually as to the best-case scenario location. In addition to the inclusion of the digitally rendered center cavity 116*b*, optimization may include changes to the dimensions of the digitally rendered base static cranial implant 112*a* and changes with regard to positioning of the functional neurosurgical implant 114*a* relative to the digitally rendered base static cranial implant 112*a*. The goal is to design a low-profile intercranial device 10 so that there will be no need for any intra-operative modification of the low-profile intercranial device 10. This offers a valuable advance allowing for up to 1-2 hours of time saving. In addition, and because of the non-changeable and fixed in shape/size/contour of the functional neurosurgical implant 14 used in accordance with the present invention, the present low-profile intercranial device 10 exhibits all the advantages of pre-operative and intra-operative plasticity related to shape, contour and size by integrating the unmodified functional neurosurgical implant 14 into the customized static cranial implant 12.

Figure 8:
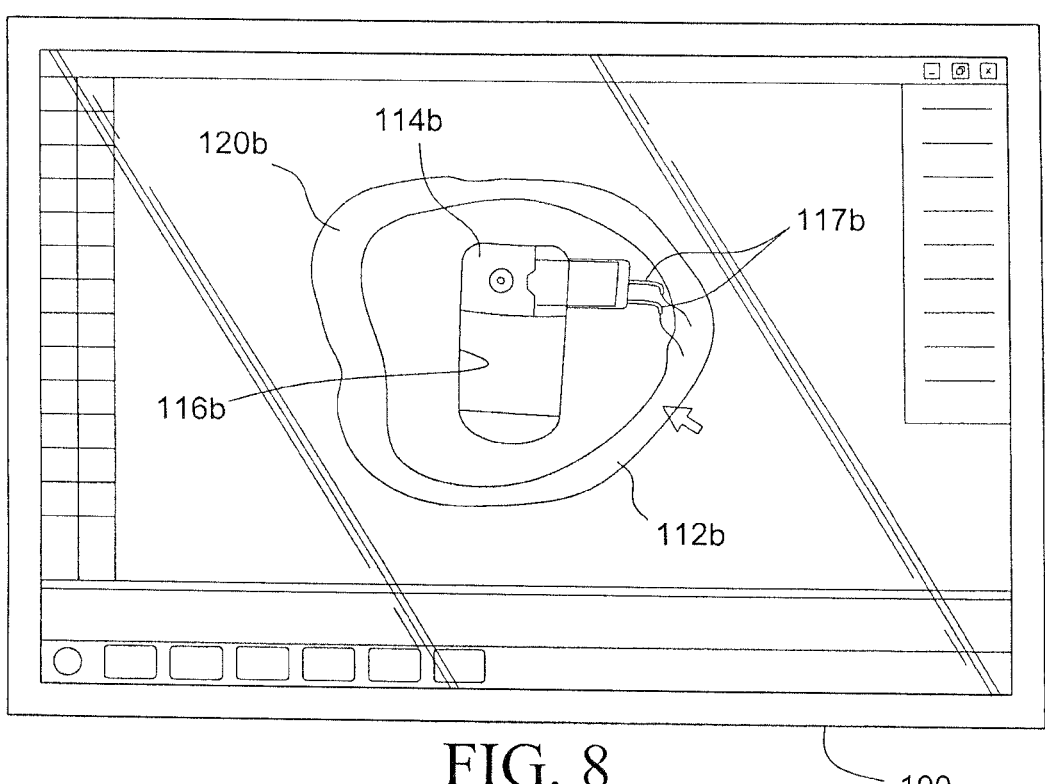
FIG. 8 is a computer screenshot showing an optimized hybrid rendering in accordance with the present invention.

As shown in FIG. 8, The optimized digitally rendered functional neurosurgical implant 114*b* and the optimized digitally rendered customized static cranial implant 112*b* are optimized such that the final physical functional neurosurgical implant 14 will have a "key-in-lock" type (that is, a closely conforming or high tolerance) fit within the final physical customized static cranial implant 12. This optimization results in the optimized hybrid rendering 120*b* composed of the optimized digitally rendered functional neurosurgical implant 114*b* and the optimized digitally rendered customized static cranial implant 112*b*.

The optimized hybrid rendering 120*b* offers both pre-operative virtual assessment of the relationship optimized digitally rendered functional neurosurgical implant 114*b* and an optimized digitally rendered customized static cranial implant 112*b*, as well as pre-operative optimization of the physical low-profile intercranial device 10 via known laser-cutting devices facilitated via surgical robot-assisted technologies (or by hand where such capabilities are not available). Both steps help to strengthen the chances that the relationship of customized static cranial implant 12 and the functional neurosurgical implant 14 will be optimized down to submillimeter accuracy. Depending upon the needs of the patient, the structure of the optimized digitally rendered customized static cranial implant 112*b*, and the specifics of the optimized digitally rendered functional neurosurgical implant 114*b*, the optimized digitally rendered functional neurosurgical implant 114*b* and the optimized digitally rendered customized static cranial implant 112*b* (as well as the resulting low-profile intercranial device 10 produced as a result of these renderings) will likely have many desired features (for improved safety and aesthetic outcomes relative to the patient appearance), such as, linear channels formed within the customized static cranial implant 12 for wires to tunnel through, pockets within the customized static cranial implant 12 to pack excess wire length, access holes within the customized static cranial implant 12 for battery replacement, etc.

Once the optimized digitally rendered functional neurosurgical implant 114*b* and the optimized digitally rendered customized static cranial implant 112*b* are virtually matched, the anatomical aspects will be ideal for patient-specific needs and the optimized hybrid rendering 120*b* (saved as an STL (or other digital format)) file is then used to manufacture the present low-profile intercranial device 10 which may ultimately be assembled with the functional neurosurgical implant 14 positioned with center cavity 16 of the customized static cranial implant 12.

In particular, with the STL (or other digital format) file of the optimized hybrid rendering 120*b* of the customized static cranial implant 12 and the functional neurosurgical implant 14, conventional manufacturing techniques are used to fabricate and laser cut the customized static cranial implant 12 and the functional neurosurgical implant 14 with robot-assistance for extreme accuracy (see PCT Publication No. WO 2016/086049, based upon PCT Application No. PCT/US2015/62516, entitled "A CUTTING MACHINE FOR RESIZING RAW IMPLANTS DURING SURGERY,"), as compared to commonly-employed, human hand modification. For example, the customized static cranial implant 12 can be obtained in "non-sterile form" from any of the dozens of FDA-approved companies in existence nationwide that are capable of producing cranial implants in accordance with the requirement of the optimized digitally rendered customized static cranial implant 112*b*. A functional neurosurgical implant 14 corresponding to the optimized digitally rendered functional neurosurgical implant 114*b* may be purchased from appropriate vendors with or without FDA approval.

It is also appreciated that the customized static cranial implant 12 and/or the functional neurosurgical implant 14 may be produced through the use of 3-D digital printing technology 400 (see FIG. 26). With this in mind, and in addition to distinctly separate functional neurosurgical implants 14, the functional neurosurgical implant or portions thereof may be integrated into the customized static cranial implant through three-dimensional printing. With the use of three-dimensional printing electronic circuitry employed by the functional neurosurgical implant may be created directly on the surfaces of the customized static cranial implant in a manner optimally utilizing the space available for the remaining portions of the functional neurosurgical implant. Similarly, vital nervous system components may be printed into the customized static cranial implant or non-clear bony structures designed to resolve complex disabilities may be printed into the customized static cranial implant. For example, the functional neurosurgical implant or portions thereof may be three-dimensionally printed within the center cavity. Where the two-piece embodiment as described above is employed, the functional neurosurgical implant or portions thereof may be three-dimensionally printed on the center recess of the base cranial implant member or the cover cranial implant member. In another embodiment, the customized cranial implant and the printable components of the functional neurosurgical implant may be printed in a single print process taking advantage of the three-dimensional printing system's ability to print multiple materials during a single print job. Ultimately, the application of three-dimensional printing in accordance with the present invention allows immensely complex systems to be compacted into the space needed in the replacement of cranial bones.

It is also appreciated robot-assisted methodologies for implant modification may be used to optimize accuracy by employing laser-cutting methods as described in PCT Publication No. WO 2016/086049, based upon PCT Application No. PCT/US2015/62516, entitled "A CUTTING MACHINE FOR RESIZING RAW IMPLANTS DURING SURGERY". Such optimization of the physical low-profile intercranial device 10 may take place pre-operatively via existing laser-cutting devices facilitated via surgical robot-assisted technologies and navigation-based technologies (for example, da Vinci® surgical system, Mako® robotic-arm surgical system, and the Johns Hopkins system described in PCT Publication No. WO 2016/086049, based upon PCT Application No. PCT/US2015/62516, entitled "A CUTTING MACHINE FOR RESIZING RAW IMPLANTS DURING SURGERY,"), as well as via future surgical robot-assisted and surgical navigation-based technologies that become available. It is further appreciated optimization of the physical low-profile intercranial device 10 may also be achieved intra-operatively as required by making such technologies available within (or adjacent to) the operating room by using a laser-cutting robot in the operating room to perform real-time modifications of the static cranial implant modification for ideal interdigitation with the functional neurologic implant.

By way of example, the customized static cranial implant 12 is created by first using a 3-D printed model of the optimized digitally rendered customized static cranial implant 112b, which is then molded with a hard plastic model. With this mold in hand, the customized static cranial implant 12 is fabricated with a liquid material, for example a clear PMMA as discussed above. Once cured and solid, processed and sterilized, the customized static cranial implant 12 will be complete, but may be pre-operatively modified by robot and/or laser (or manually where such robot controlled lasers are not available) to help optimize its position alongside the functional neurosurgical implant 14.

The customized static cranial implant 12 will commonly be in the shape of the resected portion of the patient's original cranium but with a negative space (that is, the center cavity 16 (or cavities where required)) exactly the shape of the functional neurosurgical implant 14 (or implants) hollowed out. The present low-profile intercranial device 10 is the first-ever such medical device to provide a hollowed-out customized static cranial implant 12 capable of "accepting" a neighboring functional neurosurgical implant 14 with ideal shape and form amongst the two. Essentially, the functional neurosurgical implant 14 is the "male" component and the customized static cranial implant 12 is the "female" component—and together they are in exact harmony thereby improving surgical outcomes and ultimate patient satisfaction.

By manufacturing the present low-profile intercranial device 10 in this manner, the final physical components of the low-profile intercranial device 10, that is, the customized static cranial implant 12 and the functional neurosurgical implant 14 are virtually matched pre-operatively such that the resulting low-profile intercranial device 10 is ideally constructed to drastically minimize the risk of scalp pain, scalp contour irregularities, extrusion of implant through scalp, painful scalp syndrome, visual craniofacial deformity, and infection secondary to micromotion of foreign materials, and/or brain injuries when being placed underneath the skull.

Figures 16, 17:
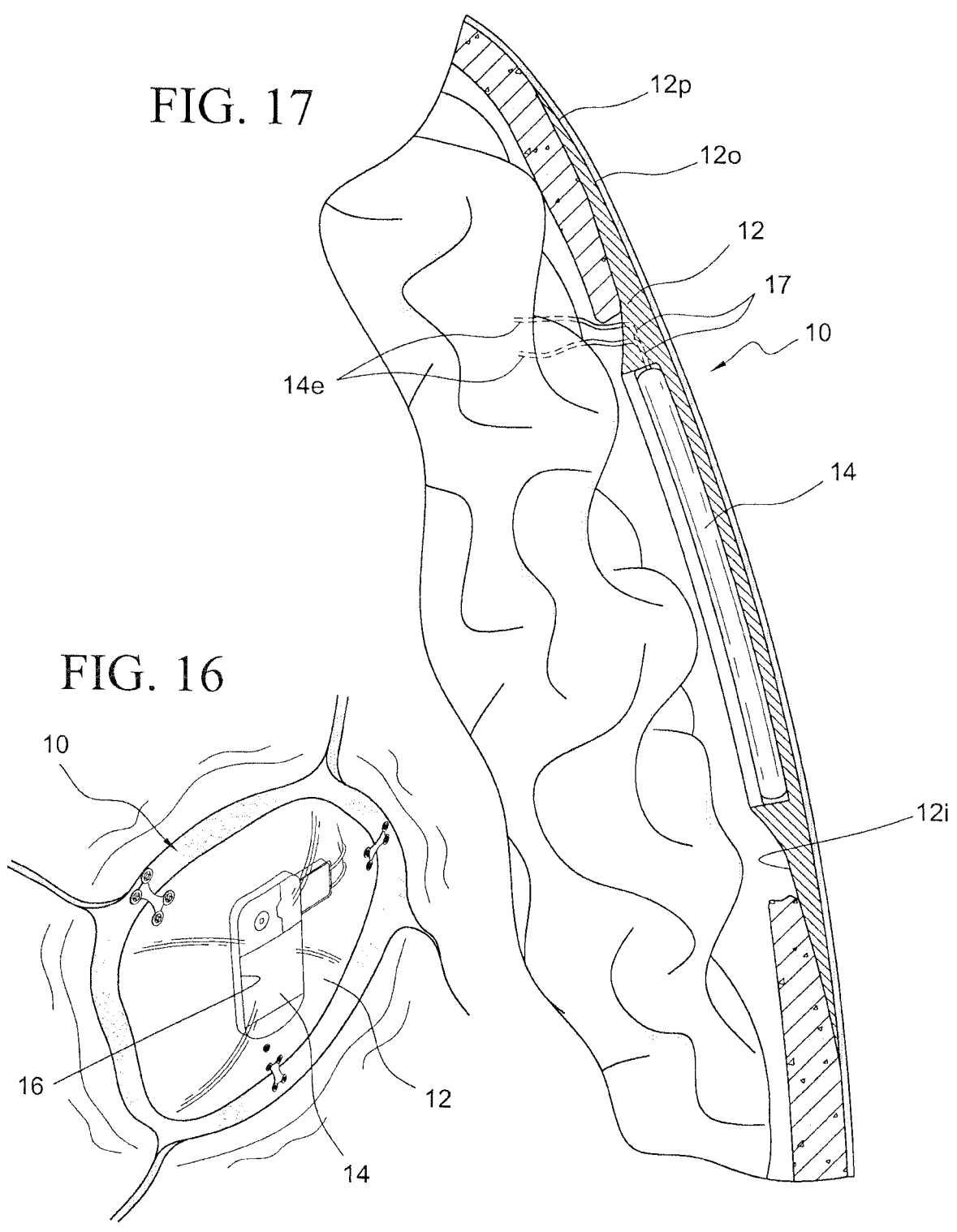
FIG. 16 is an installed perspective view of the low-profile intercranial device shown in FIG. 1.
FIG. 17 is a sectional view of the low-profile intercranial device shown in FIG. 16.
Figures 18, 19:
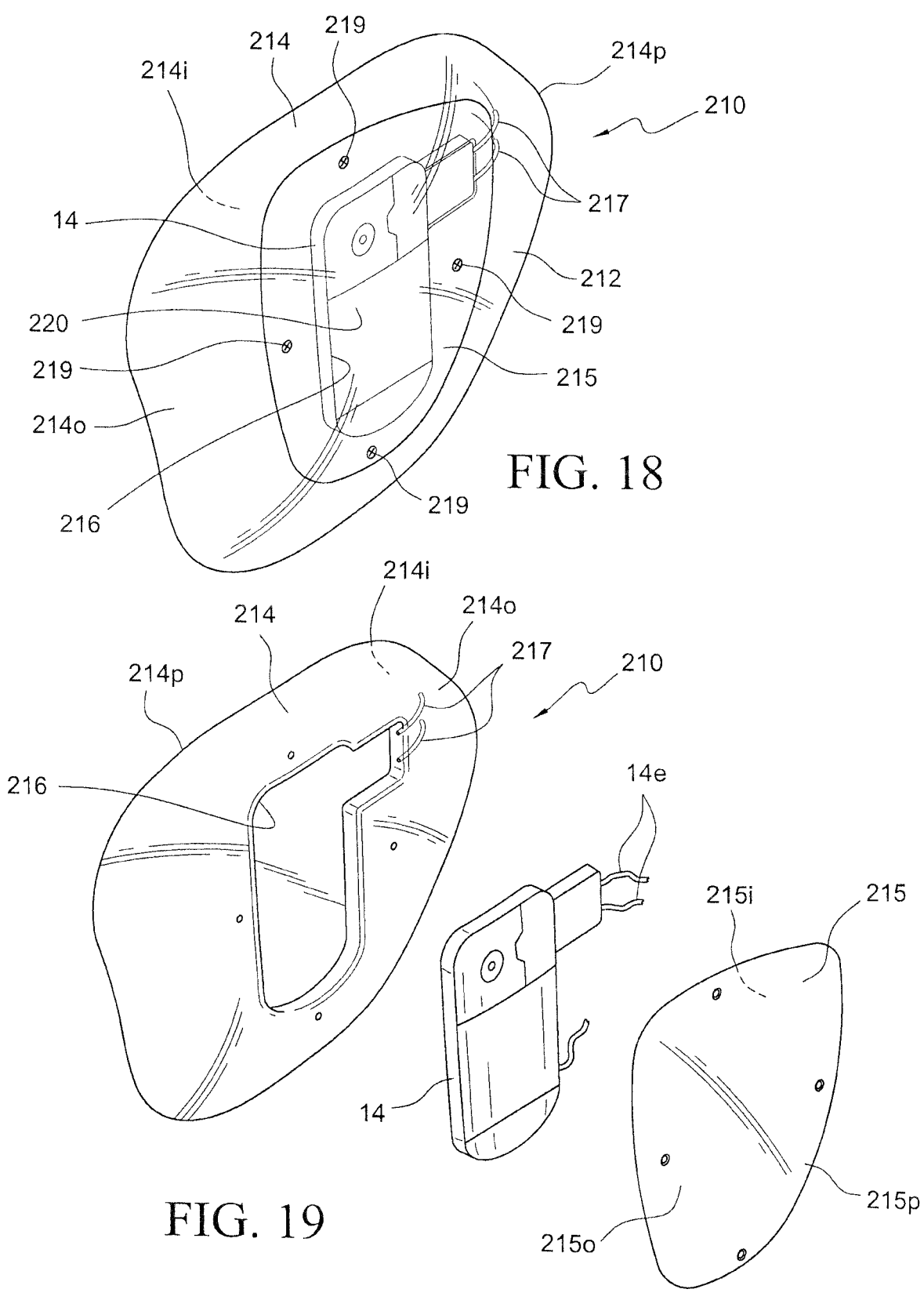
FIG. 18 is a perspective view of a low-profile intercranial device in accordance with an alternate embodiment wherein the customized static cranial implant is of a two-piece construction.
FIG. 19 is an exploded view of the low-profile intercranial device shown in FIG. 18.
Figures 20, 21:
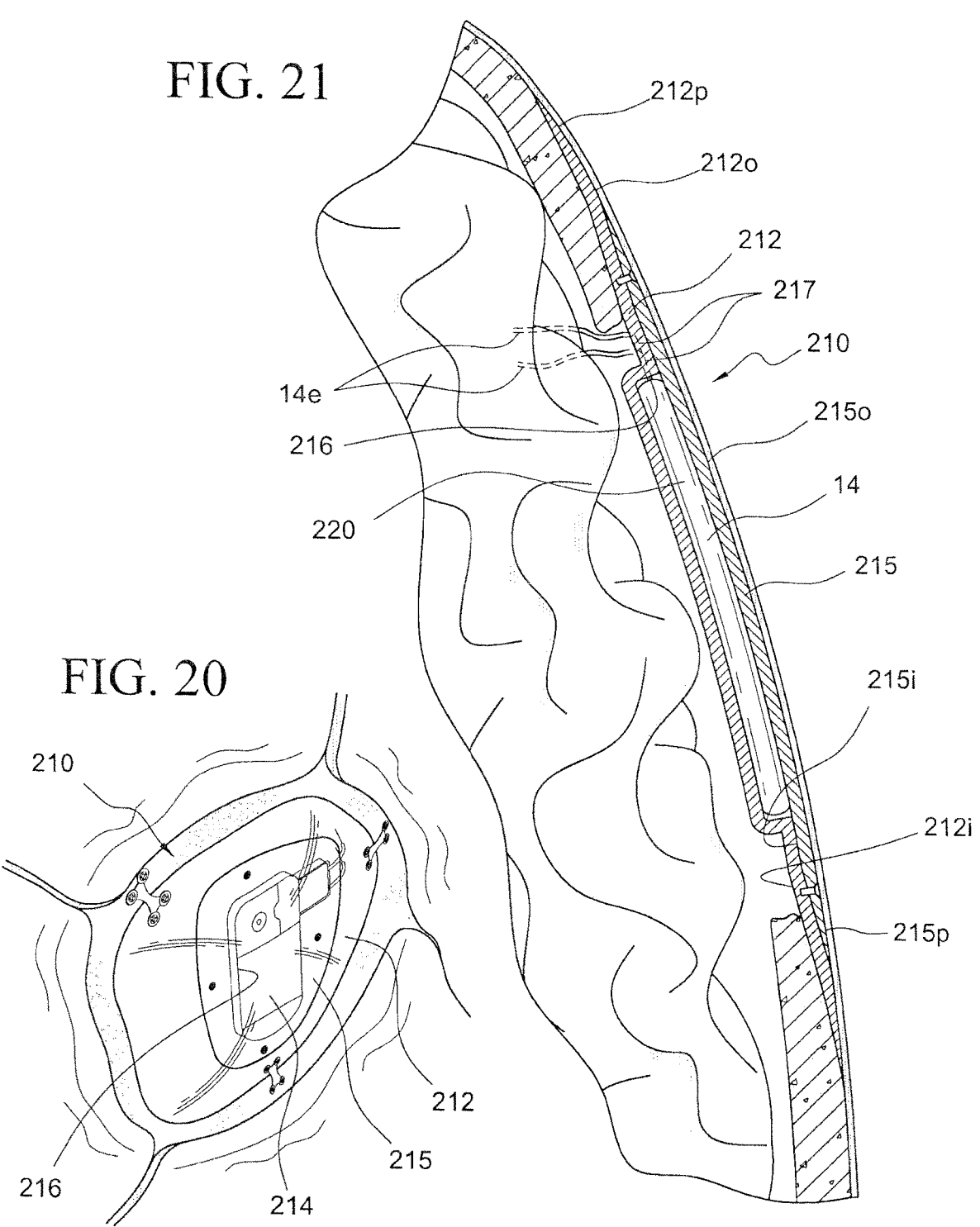
FIG. 20 is an installed perspective view of the low-profile intercranial device shown in FIG. 18.
FIG. 21 is a sectional view of the low-profile intercranial device shown in FIG. 20.

With the low-profile intercranial device 10 fully fabricated and assembled, that is, the functional neurosurgical implant 14 positioned within the center cavity 16 of the customized static cranial implant 12, the low-profile intercranial device 10 is positioned within the intercranial space so as to replace the resected portion of the cranium (see FIGS. 16 and 17 for the one-piece customized static cranial implant embodiment and FIGS. 20 and 21 for the two-piece customized static cranial implant embodiment).

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A cranial device, comprising:
a cranial implant shaped and dimensioned for placement at least partially within a resected portion of a patient's skull during performance of a cranioplasty, wherein the cranial implant is clear and allows for ultrasound transmission through the cranial implant for transmission of vital imaging with minimal distortion and wireless signal communication; and
the cranial implant including an outer first surface, an inner second surface, and a peripheral edge extending between the outer first surface and the inner second surface, the cranial implant further including a cavity formed in the cranial implant, the cavity being shaped and dimensioned to receive a functional neurosurgical implant;
the cranial implant comprises a base cranial implant member and a cover cranial implant member, the base cranial implant member including an outer convex first surface, an inner second surface, and a peripheral edge extending between the outer convex first surface and the inner second surface, the base cranial implant member including a recess formed in the outer convex first surface thereof, the recess having side walls and a bottom, the recess being shaped and dimensioned to receive the functional neurosurgical implant; and the cover cranial implant member fits over the recess along the outer convex first surface of the base cranial implant member and is shaped and dimensioned for selective placement over the recess to define the cavity in which the functional neurosurgical implant may be positioned, the cover cranial implant member including an outer convex first surface, an inner second surface, and a peripheral edge shaped and dimensioned for engagement with the outer convex first surface of the base member along an entirety of a periphery of the recess of the base member such that the outer first surface of the cranial implant consists essentially of the outer convex first surface of the cover cranial implant member and that portion of the outer convex first surface of the base cranial implant member not covered by the cover cranial implant member, wherein the inner second surface of the cover cranial implant member and the outer first surface of the base cranial implant member along the center recess define the cavity configured to conform to requirements of the functional neurosurgical implant, and that portion of the outer convex first surface of the base cranial implant member not covered by the cover cranial implant member extends to the peripheral edge of the base cranial implant member exhibiting a shape conforming to the resected portion of the skull; and
a functional neurosurgical implant positioned in the cavity.

2. The cranial device according to claim 1, wherein the cranial implant is made of clear polymethyl methacrylate (PMMA).

3. The cranial device according to claim 2, wherein the cranial implant allows for wireless optical links between the functional neurosurgical implant and remote devices or for power transmission and/or receipt between the functional neurosurgical implant and devices outside of the cranial implant.

4. The cranial device according to claim 2, wherein the cranial implant allows for radio-frequency (RF) transmission through the cranial implant.

5. The cranial device according to claim 1, wherein the cranial implant is a custom cranial implant.

6. A cranial device, comprising:

a cranial implant shaped and dimensioned for placement at least partially within a resected portion of a patient's skull during performance of a cranioplasty, the cranial implant allowing for transmission of ultrasound waves therethrough;

the cranial implant including an outer first surface, an inner second surface, and a peripheral edge extending between the outer first surface and the inner second surface, the cranial implant further including a cavity formed in the cranial implant, the cavity being shaped and dimensioned to receive a functional neurosurgical implant providing for ultrasound functionality; and the cranial implant comprises a base cranial implant member and a cover cranial implant member, the base cranial implant member including an outer convex first surface, an inner second surface, and a peripheral edge extending between the outer convex first surface and the inner second surface, the base cranial implant member including a recess formed in the outer convex first surface thereof, the recess having side walls and a bottom, the recess being shaped and dimensioned to receive the functional neurosurgical implant; and the cover cranial implant member fits over the recess along the outer convex first surface of the base cranial implant member and is shaped and dimensioned for selective placement over the recess to define the cavity in which the functional neurosurgical implant may be positioned, the cover cranial implant member including an outer convex first surface, an inner second surface, and an entirety of a peripheral edge shaped and dimensioned for engagement with the outer convex first surface of the base member along a periphery of the recess of the base member such that the outer first surface of the cranial implant consists essentially of the outer convex first surface of the cover cranial implant member and that portion of the outer convex first surface of the base cranial implant member not covered by the cover cranial implant member, wherein the inner second surface of the cover cranial implant member and the outer first surface of the base cranial implant member along the center recess define the cavity configured to conform to requirements of the functional neurosurgical implant, and that portion of the outer convex first surface of the base cranial implant member not covered by the cover cranial implant member extends to the peripheral edge of the base cranial implant member exhibiting a shape conforming to the resected portion of the skull; and a functional neurosurgical implant with ultrasound functionality positioned in the cavity.

7. The cranial device according to claim 6, wherein the cranial implant is a custom cranial implant.

8. The cranial device according to claim 6, wherein the cranial implant is made of clear polymethyl methacrylate (PMMA).

9. The cranial device according to claim 6, wherein the cover cranial implant member is removably securable to the base cranial implant member.

10. A cranial device, comprising:

a radiolucent cranial implant shaped and dimensioned for placement at least partially within a resected portion of a patient's skull;

the cranial implant including an outer first surface, an inner second surface, and a peripheral edge extending between the outer first surface and the inner second surface, the cranial implant further including a cavity formed in the cranial implant, the cavity being shaped and dimensioned to receive a functional neurosurgical implant; and the cranial implant comprises a base cranial implant member and a cover cranial implant member, the base cranial implant member including an outer convex first surface, an inner second surface, and a peripheral edge extending between the outer convex first surface and the inner second surface, the base cranial implant member including a recess formed in the outer convex first surface thereof, the recess having side walls and a bottom, the recess being shaped and dimensioned to receive the functional neurosurgical implant; and the cover cranial implant member fits over the recess along the outer convex first surface of the base cranial implant member and is shaped and dimensioned for selective placement over the recess to define the cavity in which the functional neurosurgical implant may be positioned, the cover cranial implant member including an outer convex first surface, an inner second surface, and an entirety of a peripheral edge shaped and dimensioned for engagement with the outer convex first surface of the base member along a periphery of the recess of the base member, such that the outer first surface of the cranial implant consists essentially of the outer convex first surface of the cover cranial implant member and that portion of the outer convex first surface of the base cranial implant member not covered by the cover cranial implant member, wherein the inner second surface of the cover cranial implant member and the outer first surface of the base cranial implant member along the center recess define the cavity configured to conform to requirements of the functional neurosurgical implant, and that portion of the outer convex first surface of the base cranial implant member not covered by the cover cranial implant member extends to the peripheral edge of the base cranial implant member exhibiting a shape conforming to the resected portion of the skull; and a functional neurosurgical implant with radio-frequency (RF) functionality positioned in the cavity.

11. The cranial device according to claim 10, wherein the cranial implant is a custom cranial implant.

12. The cranial device according to claim 10, wherein the cranial implant is made of clear polymethyl methacrylate (PMMA).

* * * * *